(12) United States Patent
Egawa et al.

(10) Patent No.: US 8,252,433 B2
(45) Date of Patent: *Aug. 28, 2012

(54) QUINOXALINE DERIVATIVE, AND LIGHT-EMITTING DEVICE, ELECTRONIC DEVICE USING THE QUINOXALINE DERIVATIVE

(75) Inventors: Masakazu Egawa, Tochigi (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,064

(22) Filed: Apr. 25, 2011

(65) Prior Publication Data
US 2011/0198574 A1    Aug. 18, 2011

Related U.S. Application Data

(63) Continuation of application No. 11/859,387, filed on Sep. 21, 2007, now Pat. No. 7,931,974.

(30) Foreign Application Priority Data

Sep. 29, 2006   (JP) .................................. 2006-266159

(51) Int. Cl.
*H01L 51/54* (2006.01)
*C09K 11/00* (2006.01)

(52) U.S. Cl. ........ 428/690; 428/917; 313/504; 313/506; 252/301.16; 257/40; 257/88; 257/E51.051; 548/440; 544/349; 544/353

(58) Field of Classification Search ........... 257/E51.051; 548/440
See application file for complete search history.

(56) References Cited

U.S. PATENT DOCUMENTS

| | | | |
|---|---|---|---|
| 6,229,012 B1 | 5/2001 | Hu et al. | |
| 6,670,054 B1 | 12/2003 | Hu et al. | |
| 7,612,204 B2 | 11/2009 | Egawa et al. | |
| 7,696,348 B2 | 4/2010 | Egawa et al. | |
| 7,931,974 B2 * | 4/2011 | Egawa et al. | 428/690 |
| 2005/0003232 A1 | 1/2005 | Shitagaki et al. | |
| 2005/0065342 A1 | 3/2005 | Shitagaki et al. | |
| 2005/0186446 A1 | 8/2005 | Shitagaki et al. | |
| 2007/0059553 A1 | 3/2007 | Egawa et al. | |
| 2007/0241667 A1 | 10/2007 | Ohsawa et al. | |
| 2008/0079354 A1 | 4/2008 | Egawa et al. | |
| 2008/0193794 A1 | 8/2008 | Egawa et al. | |
| 2009/0140641 A1 | 6/2009 | Nomura et al. | |
| 2009/0140642 A1 | 6/2009 | Kadoma et al. | |
| 2009/0184633 A1 | 7/2009 | Kadoma et al. | |
| 2009/0203704 A1 | 8/2009 | Kadoma et al. | |
| 2010/0069636 A1 | 3/2010 | Shitagaki et al. | |
| 2010/0141130 A1 | 6/2010 | Egawa et al. | |

FOREIGN PATENT DOCUMENTS

| | | |
|---|---|---|
| EP | 1 616 864 A1 | 1/2006 |
| WO | WO 2004/094389 A1 | 11/2004 |
| WO | WO 2005/115061 A1 | 12/2005 |
| WO | WO 2006/022193 A1 | 3/2006 |

OTHER PUBLICATIONS

Chen, S. et al, "Synthesis and Characterization of n-Type Materials for Non-Doped Organic Red-Light-Emitting Diodes," Advanced Functional Materials, vol. 15, No. 9, 2005, pp. 1541-1546.
European Search Report re application No. EP 07017781.1, dated Feb. 22, 2008.

* cited by examiner

*Primary Examiner* — Jennifer Chriss
*Assistant Examiner* — Michael H Wilson
(74) *Attorney, Agent, or Firm* — Husch Blackwell LLP

(57) ABSTRACT

The present invention provides a novel organic compound having excellent heat resistance. By using the novel organic compound, a light-emitting device and an electronic device having excellent heat resistance can be provided. A quinoxaline derivative represented by the general formula (1) is provided. Since the quinoxaline derivative represented by the general formula (1) has excellent heat resistance, when it is used for a light-emitting element, a light-emitting device using the light-emitting element also have excellent heat resistance. Further, electronic devices having excellent heat resistance can be provided.

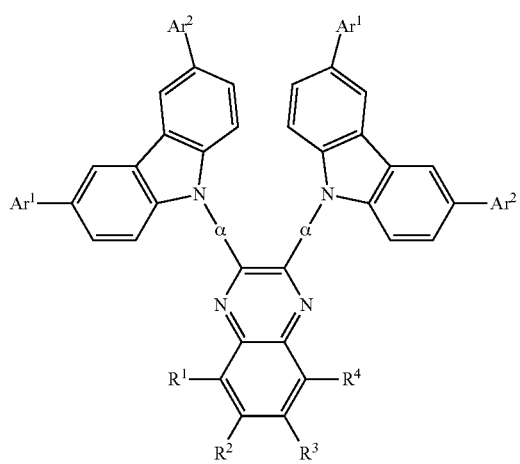

(1)

23 Claims, 16 Drawing Sheets

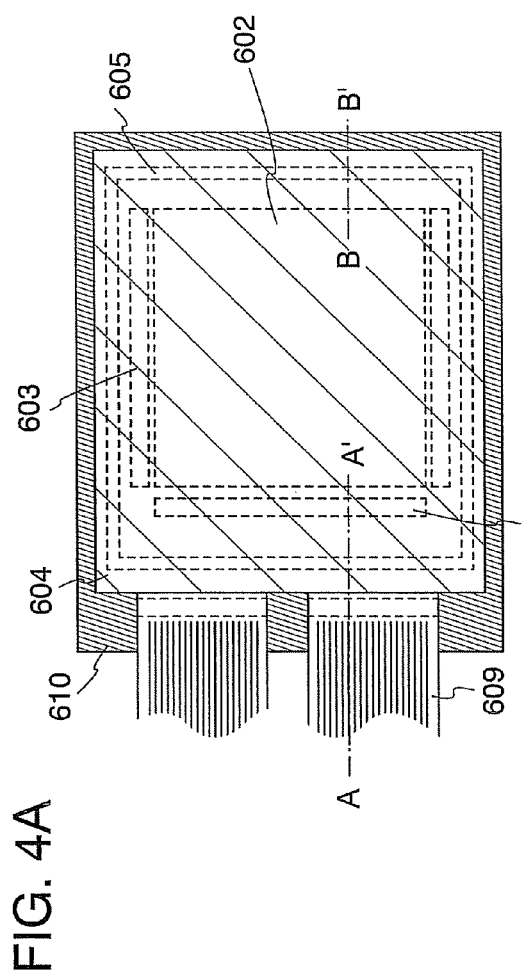
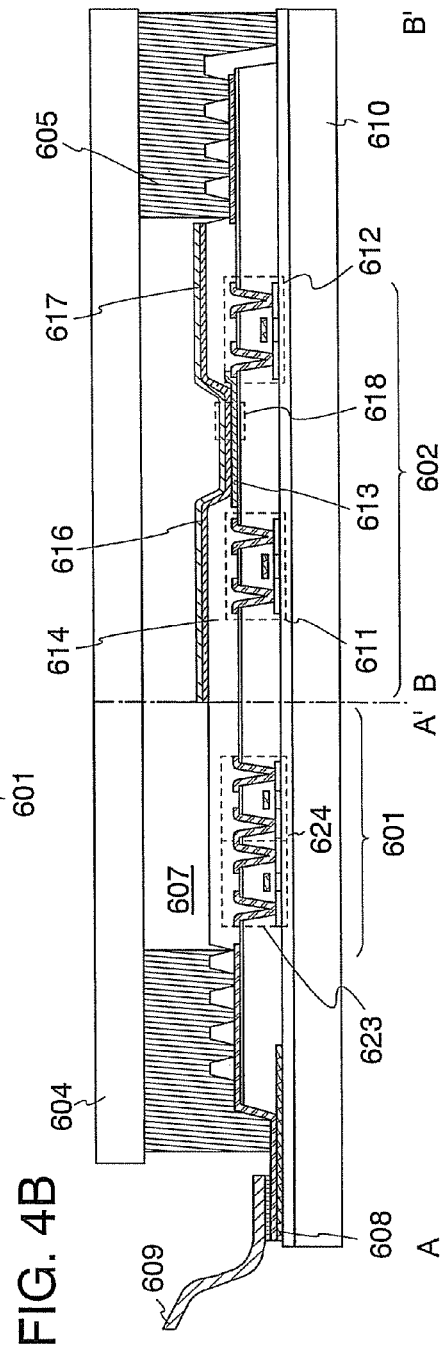
FIG. 4A
FIG. 4B

QUINOXALINE DERIVATIVE, AND LIGHT-EMITTING DEVICE, ELECTRONIC DEVICE USING THE QUINOXALINE DERIVATIVE

This application is a continuation of U.S. application Ser. No. 11/859,387 filed on Sep. 21, 2007 now U.S. Pat. No. 7,931,974.

BACKGROUND OF THE INVENTION

1. Field of the Invention

The present invention relates to quinoxaline derivatives, and light-emitting elements, light-emitting devices, electronic devices which use the quinoxaline derivatives.

2. Description of the Related Art

Organic compounds can take more various structures compared with inorganic compounds, and have possibility to provide materials having various functions by appropriate molecular design. Owing to these advantages, photo electronics and electronics which utilize functional organic materials have been attracting attention in recent years.

For example, a solar cell, a light-emitting element, an organic transistor, and the like are exemplified as electronic devices utilizing an organic compound as a functional organic material. These devices utilize electric properties and optical properties of the organic compound. Among them, in particular, a light-emitting element has been making remarkable development.

It is said that light emission mechanism of a light-emitting element is as follows: when a voltage is applied between a pair of electrodes with a light-emitting layer interposed therebetween, electrons injected from a cathode and holes injected from an anode are recombined in the light emission center of the light-emitting layer to form a molecular exciton, and energy is released to emit light when the molecular exciton makes the transition to a ground state. As excited states, a singlet excited state and a triplet excited state are known, and light emission is considered to be obtained from any of these excited states.

Such a light-emitting element has a lot of problems which depend on materials, in improving the element characteristics. In order to solve these problems, improvement of an element structure, development of a material, and the like have been carried out.

For example, WO 2004/094389 (Reference 1) discloses that a quinoxaline derivative is used for a light-emitting element.

SUMMARY OF THE INVENTION

However, a quinoxaline derivative disclosed in Reference 1, in which quinoxaline and carbazole are combined has improved heat resistance or the like, which leads to enhanced possibility of development of various organic compounds.

It is an object of the present invention to provide a novel organic compound having excellent heat resistance.

By using an organic compound of the present invention, a light-emitting element and a light-emitting device having excellent heat resistance can be provided.

Further, by using an organic compound of the present invention, an electronic device having excellent heat resistance can be provided.

An aspect of the present invention is a quinoxaline derivative represented by the general formula (1).

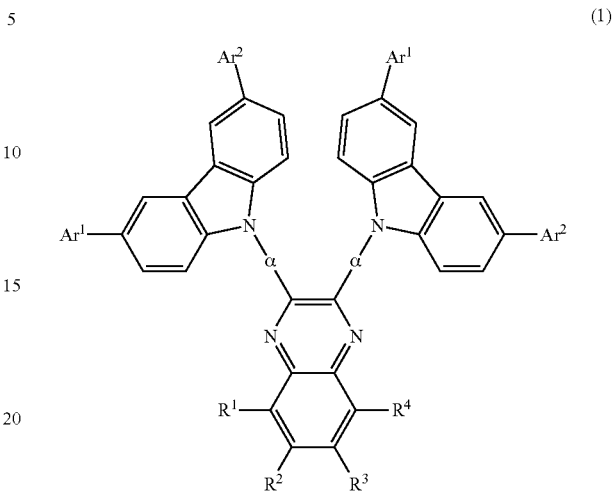

(1)

In the general formula (1), $R^1$ to $R^4$ each represent a hydrogen atom, an alkyl group having 1 to 4 carbon atoms, or an aryl group having 6 to 25 carbon atoms, and $R^1$ and $R^2$, $R^2$ and $R^3$, and $R^3$ and $R^4$ may be bound to each other to form a ring. $Ar^1$ and $Ar^2$ each represent an aryl group having 6 to 25 carbon atoms, and α represents an arylene group having 6 to 25 carbon atoms.

An aspect of the present invention is a quinoxaline derivative represented by the general formula (2).

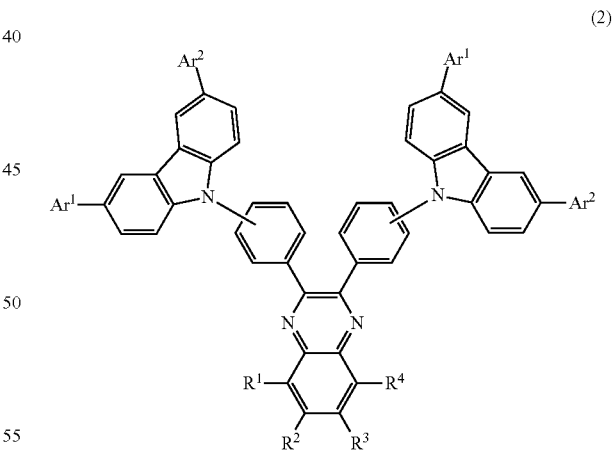

(2)

In the general formula (2), $R^1$ to $R^4$ each represent a hydrogen atom, an alkyl group having 1 to 4 carbon atoms, or an aryl group having 6 to 25 carbon atoms, and $R^1$ and $R^2$, $R^2$ and $R^3$, and $R^3$ and $R^4$ may be bound to each other to form a ring. $Ar^1$ and $Ar^2$ each represent an aryl group having 6 to 25 carbon atoms.

An aspect of the present invention is a quinoxaline derivative represented by the general formula (3).

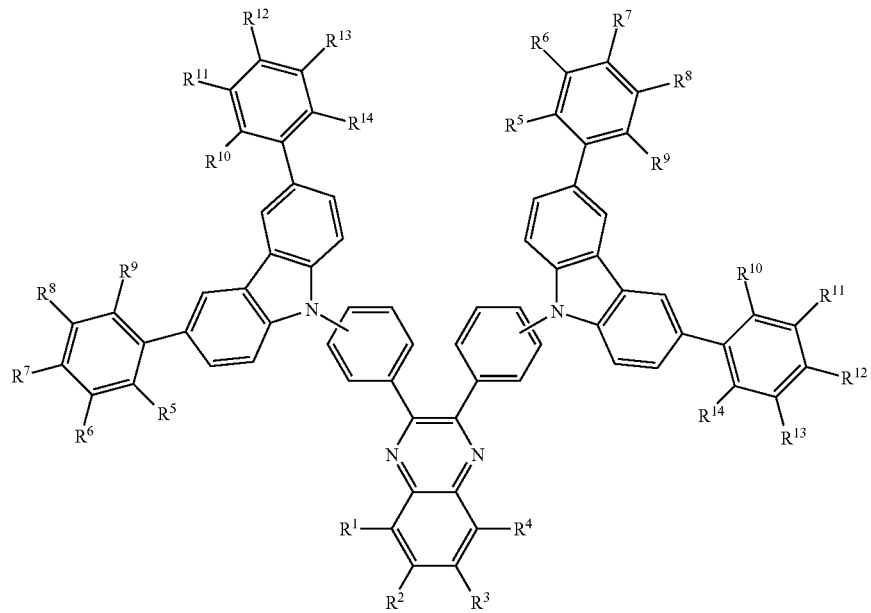

(3)

In the general formula (3), $R^1$ to $R^4$ each represent a hydrogen atom, an alkyl group having 1 to 4 carbon atoms, or an aryl group having 6 to 25 carbon atoms, and $R^1$ and $R^2$, $R^2$ and $R^3$, and $R^3$ and $R^4$ may be bound to each other to form a ring. $R^5$ to $R^{14}$ each represent a hydrogen atom, an alkyl group having 1 to 4 carbon atoms, or an aryl group having 6 to 15 carbon atoms, and $R^5$ and $R^6$, $R^6$ and $R^7$, $R^7$ and $R^8$, $R^8$ and $R^9$, $R^{10}$ and $R^{11}$, $R^{11}$ and $R^{12}$, $R^{12}$ and $R^{13}$, and $R^{13}$ and $R^{14}$ may be bound to each other to form a ring.

An aspect of the present invention is a quinoxaline derivative represented by the general formula (4).

(4)

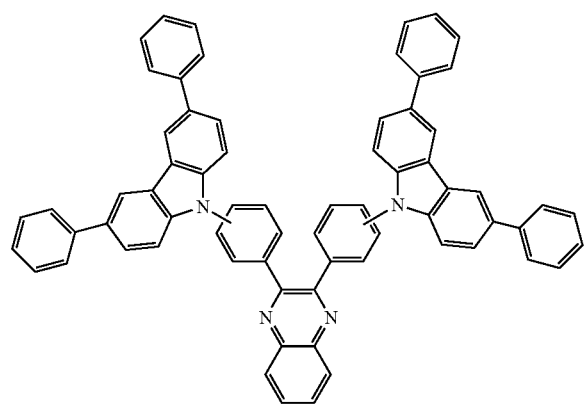

An aspect of the present invention is a quinoxaline derivative represented by the structural formula (5).

(5)

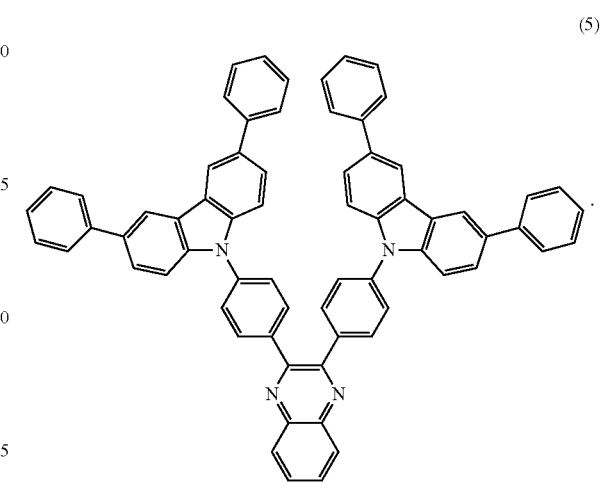

An aspect of the present invention is a light-emitting element using any of the above quinoxaline derivatives. Specifically, a light-emitting element has any of the above quinoxaline derivatives between a pair of electrodes.

An aspect of the present invention is a light-emitting element having a light-emitting layer between a pair of electrodes, and the light-emitting layer includes any of the above quinoxaline derivatives.

An aspect of the present invention is a light-emitting element having a light-emitting layer between a pair of electrodes, and the light-emitting layer includes any of the above quinoxaline derivatives and a fluorescence emitting substance.

An aspect of the present invention is a light-emitting element having a light-emitting layer between a pair of electrodes, and the light-emitting layer includes any of the above quinoxaline derivatives and a phosphorescence emitting substance.

In the above structure, the peak in the emission spectrum of the phosphorescence emitting substance is within the range of 560 nm to 700 nm.

Moreover, a light-emitting device of the present invention has a light-emitting element including a light-emitting element having any of the above quinoxaline derivatives between a pair of electrodes, and a controller for controlling light emission of the light-emitting element. It is to be noted that the light-emitting device in this specification includes an image display device, a light-emitting device, and a light source (including an illumination apparatus). Further, the light-emitting device includes various types of modules e.g., a module in which a connector such as an FPC (Flexible Printed Circuit), a TAB (Tape Automated Bonding) tape, or a TCP (Tape Carrier Package) is attached to a panel, a module in which a print wiring board is provided at an end of a TAB tape or an TCP, and a module in which an IC (Integrated Circuit) is directly mounted on a light-emitting device by a COG (Chip On Glass) method.

Electronic devices each using the light-emitting element of the present invention in its display portion are also included in the category of the present invention. Therefore, electronic devices of the present invention each have a display portion provided with the aforementioned light-emitting element and a controller for controlling light emission of the light-emitting element.

A quinoxaline derivative of the present invention has excellent heat resistance.

Since a quinoxaline derivative of the present invention has excellent heat resistance, when it is used for a light-emitting element, the light-emitting element and a light-emitting device using the light-emitting element also have excellent heat resistance.

By using a quinoxaline derivative of the present invention, an electronic device having excellent heat resistance can be provided.

BRIEF DESCRIPTION OF THE DRAWINGS

In the accompanying drawings:

FIGS. 4A and 4B illustrate a light-emitting device of the present invention;

DETAILED DESCRIPTION OF THE INVENTION

Figure 1A:
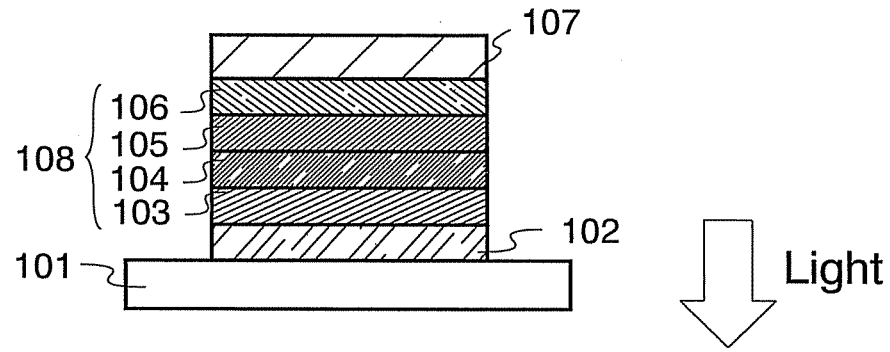
FIGS. 1A to 1C illustrate light-emitting elements of the present invention.

Embodiment modes of the present invention will now be described with reference to the drawings in detail. However, the present invention is not limited to the following description and it is easily understood by those skilled in the art that the mode and details can be variously changed without departing from the scope and spirit of the present invention. Therefore, the present invention is not construed as being limited to the description of the embodiment modes shown below.

Embodiment Mode 1

A quinoxaline derivative of the present invention is represented by the general formula (1).

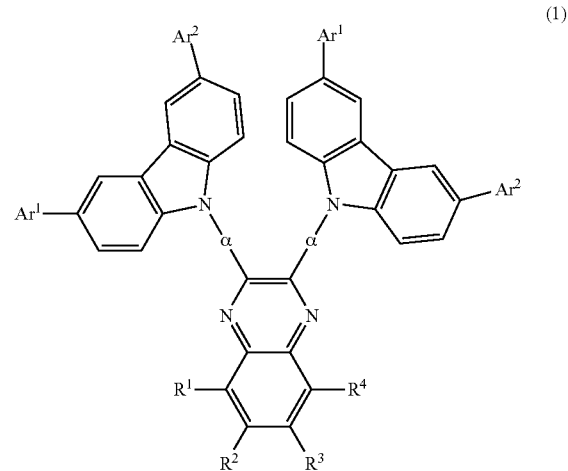

In the general formula (1), $R^1$ to $R^4$ each represent a hydrogen atom, an alkyl group having 1 to 4 carbon atoms, or an aryl group having 6 to 25 carbon atoms, and $R^1$ and $R^2$, $R^2$ and $R^3$, and $R^3$ and $R^4$ may be bound to each other to form a ring. $Ar^1$ and $Ar^2$ each represent an aryl group having 6 to 25 carbon atoms, and α represents an arylene group having 6 to 25 carbon atoms.

In particular, a quinoxaline derivative represented by the general formula (2) is preferable.

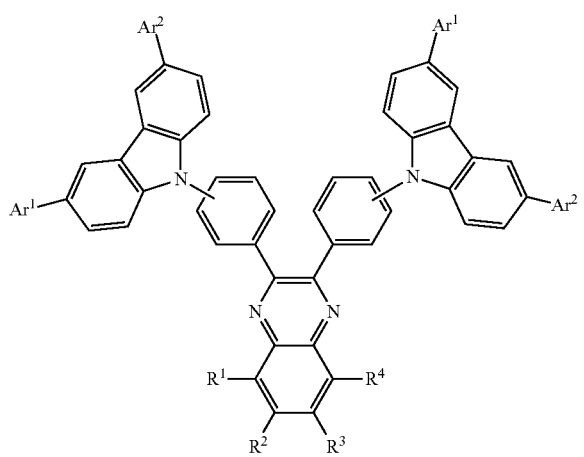

(2)

In the general formula (2), $R^1$ to $R^4$ each represent a hydrogen atom, an alkyl group having 1 to 4 carbon atoms, or an aryl group having 6 to 25 carbon atoms, and $R^1$ and $R^2$, $R^2$ and $R^3$, and $R^3$ and $R^4$ may be bound to each other to form a ring. $Ar^1$ and $Ar^2$ each represent an aryl group having 6 to 25 carbon atoms.

In particular, a quinoxaline derivative represented by the general formula (3) is preferable.

In the general formula (3), $R^1$ to $R^4$ each represent a hydrogen atom, an alkyl group having 1 to 4 carbon atoms, or an aryl group having 6 to 25 carbon atoms, and $R^1$ and $R^2$, $R^2$ and $R^3$, and $R^3$ and $R^4$ may be bound to each other to form a ring. $R^5$ to $R^{14}$ each represent a hydrogen atom, an alkyl group having 1 to 4 carbon atoms, or an aryl group having 6 to 15 carbon atoms, and $R^5$ and $R^6$, $R^6$ and $R^7$, $R^7$ and $R^8$, $R^8$ and $R^9$, $R^{10}$ and $R^{11}$, $R^{11}$ and $R^{12}$, $R^{12}$ and $R^{13}$, and $R^{13}$ and $R^{14}$ may be bound to each other to form a ring.

In particular, a quinoxaline derivative represented by the general formula (4) is preferable.

(4)

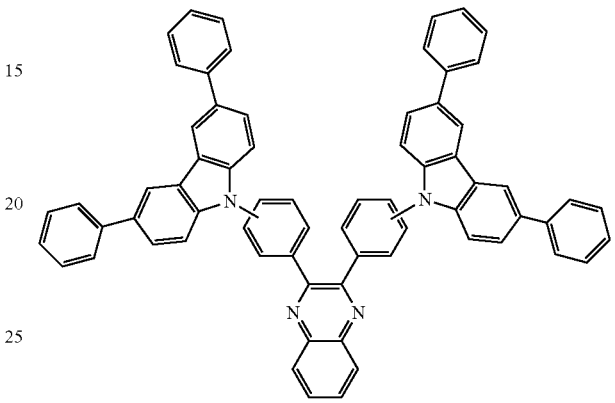

In particular, a quinoxaline derivative represented by the structural formula (5) is preferable.

(3)

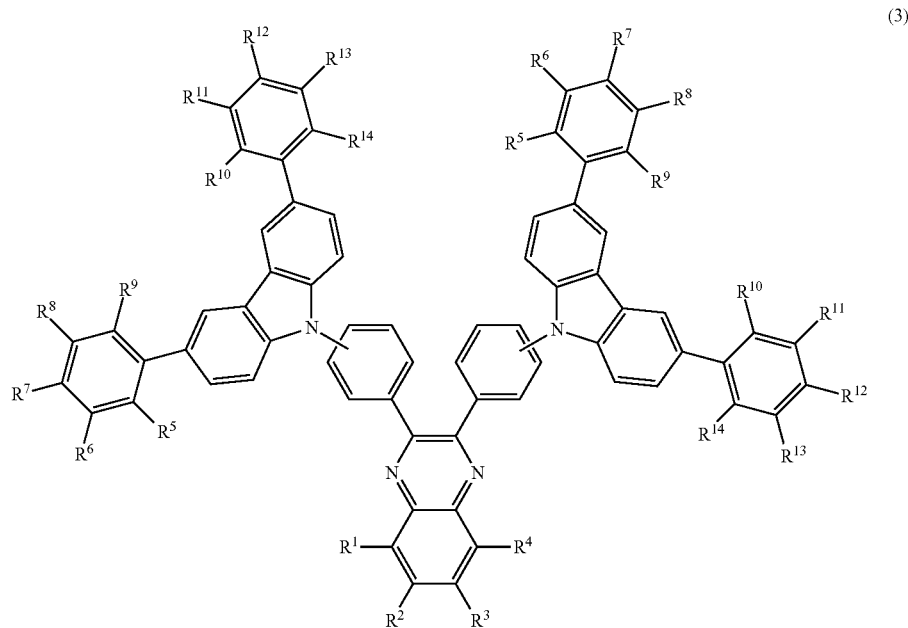

(5)
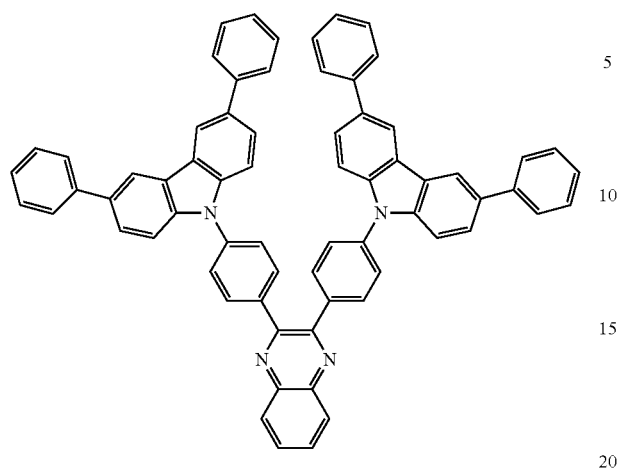
Specific examples of quinoxaline derivatives of the present invention can be quinoxaline derivatives represented by the above structural formula (5) and the following structural formulas (6) to (40). However, the present invention is not limited to these examples.
(6)
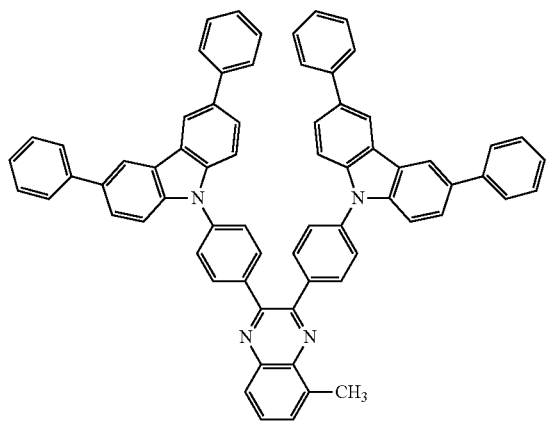
(7)
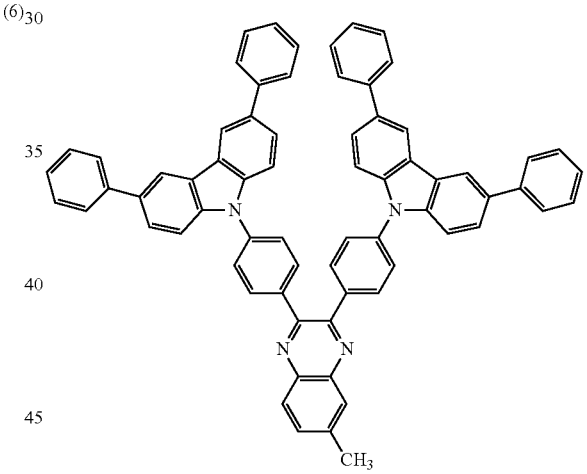
(8)
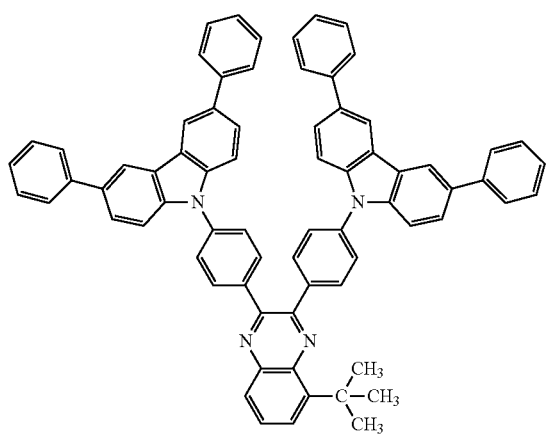
(9)
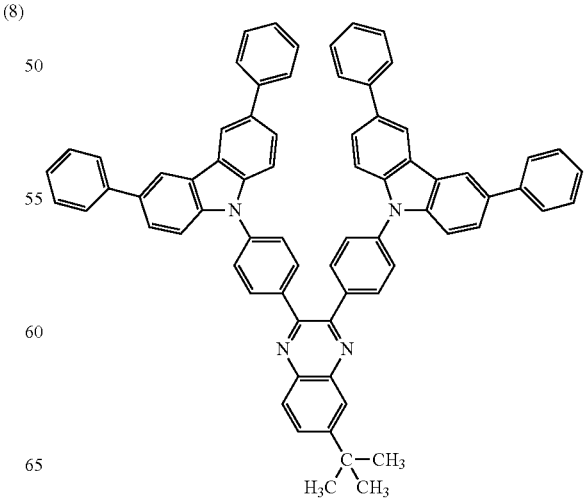

-continued
(10)
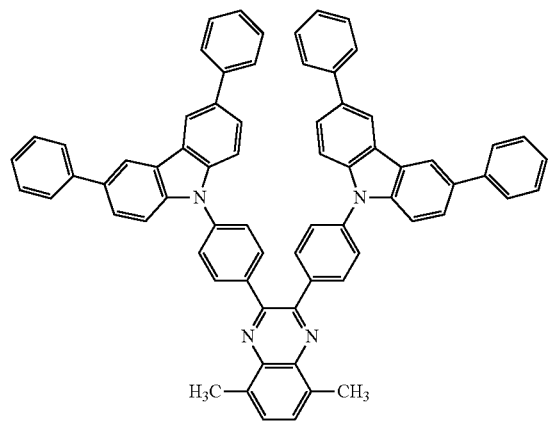
(11)
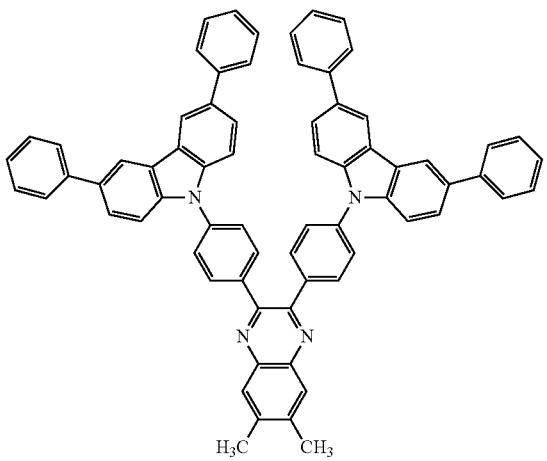
(12)
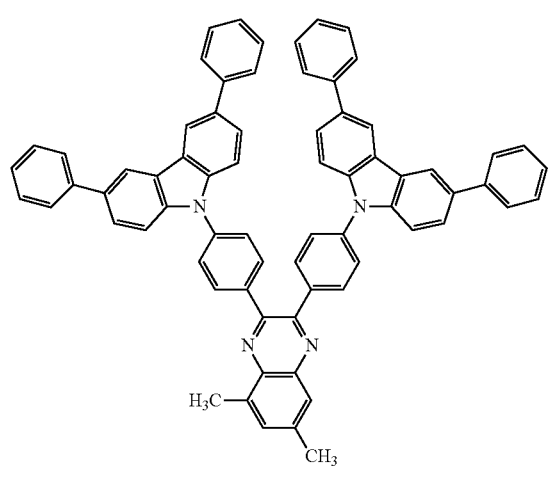
(13)
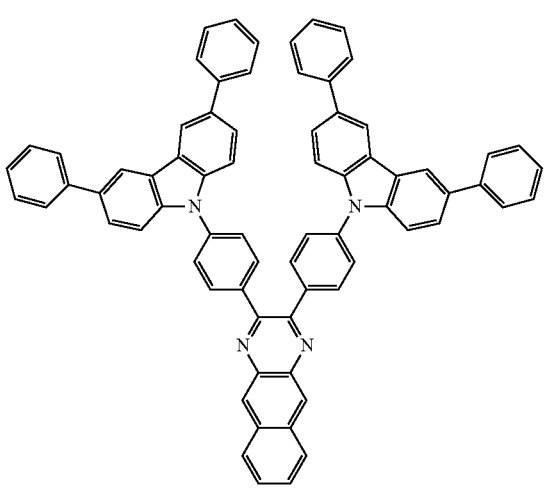
(14)
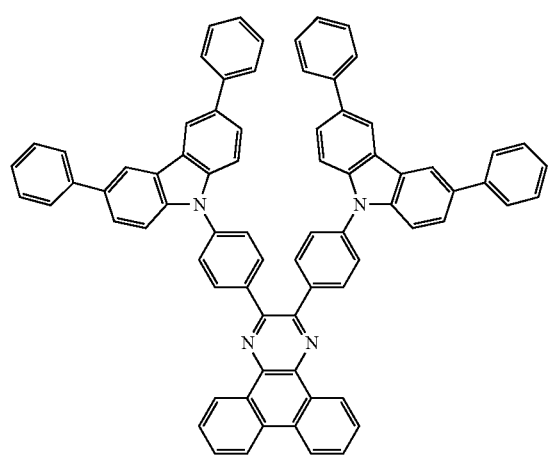
(15)
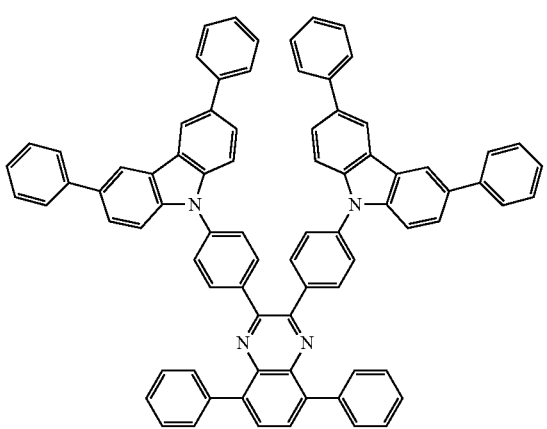

-continued
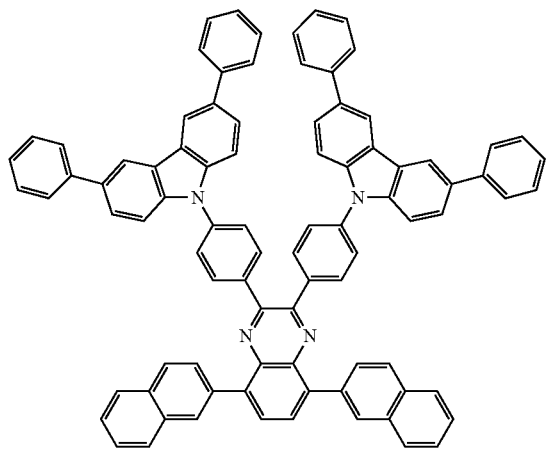
(16)
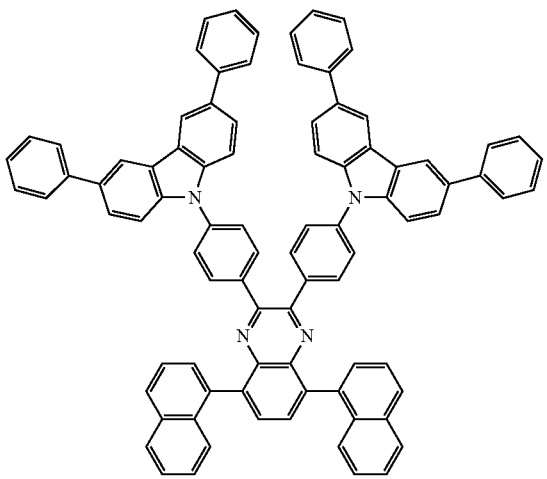
(17)
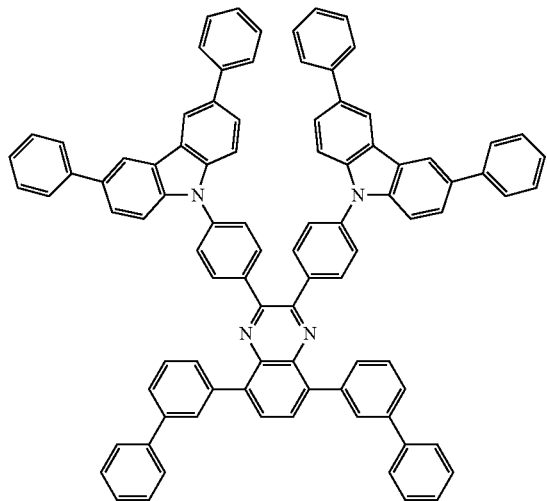
(18)
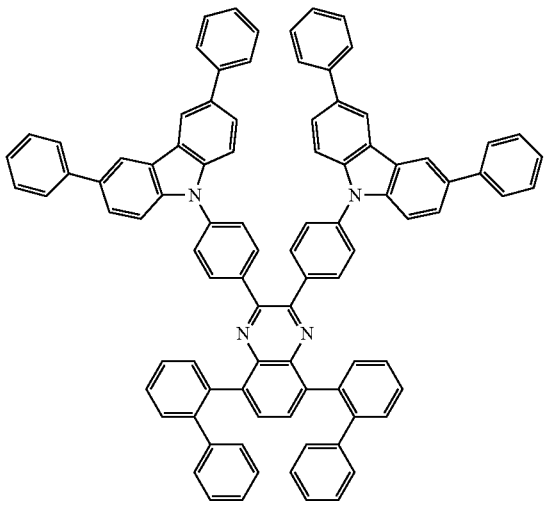
(19)
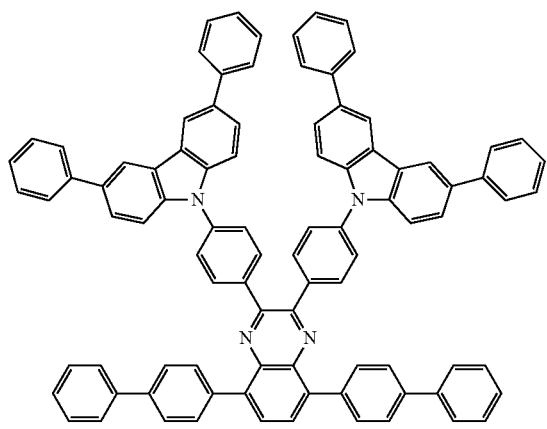
(20)
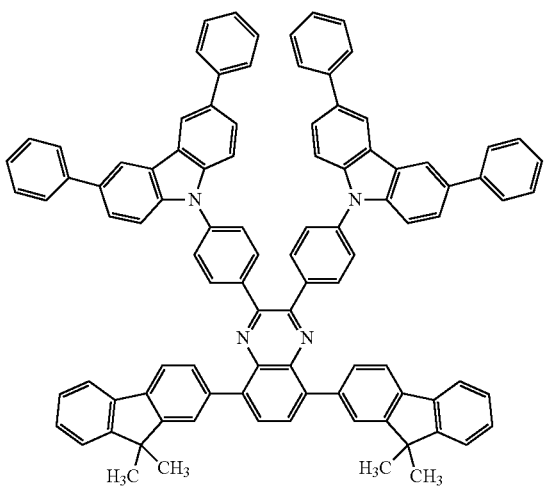
(21)

(22)
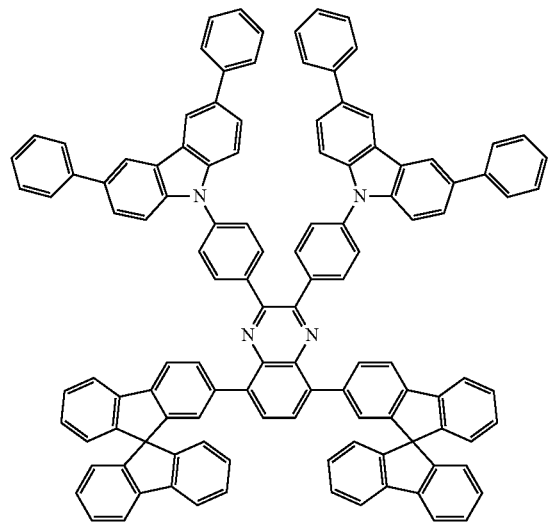
(23)
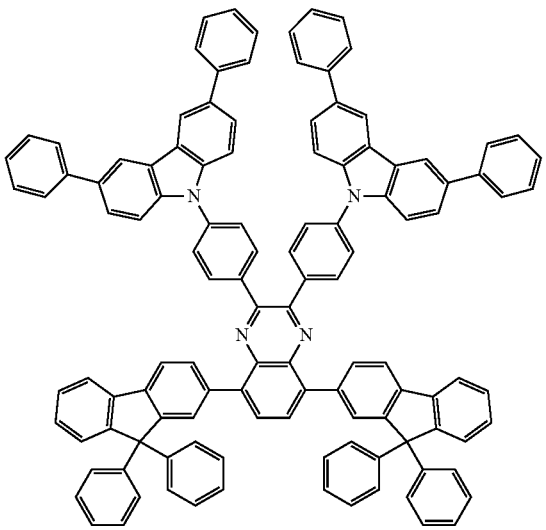
(24)
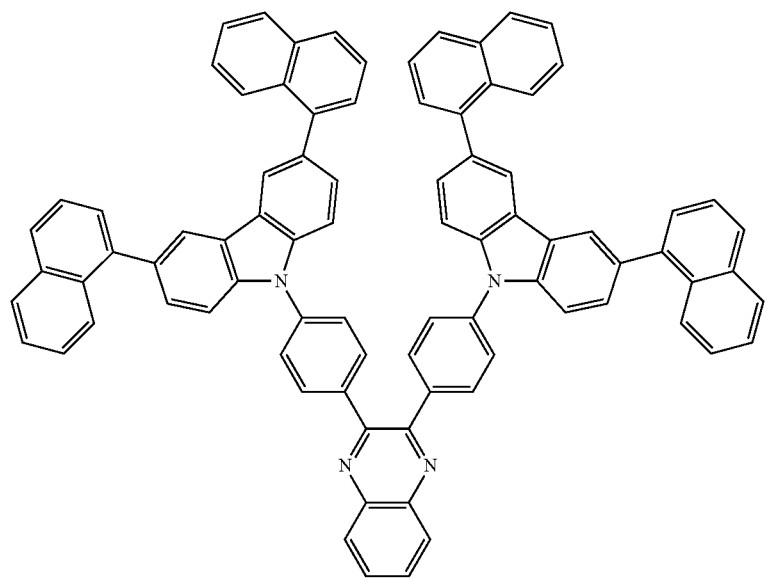

(25)
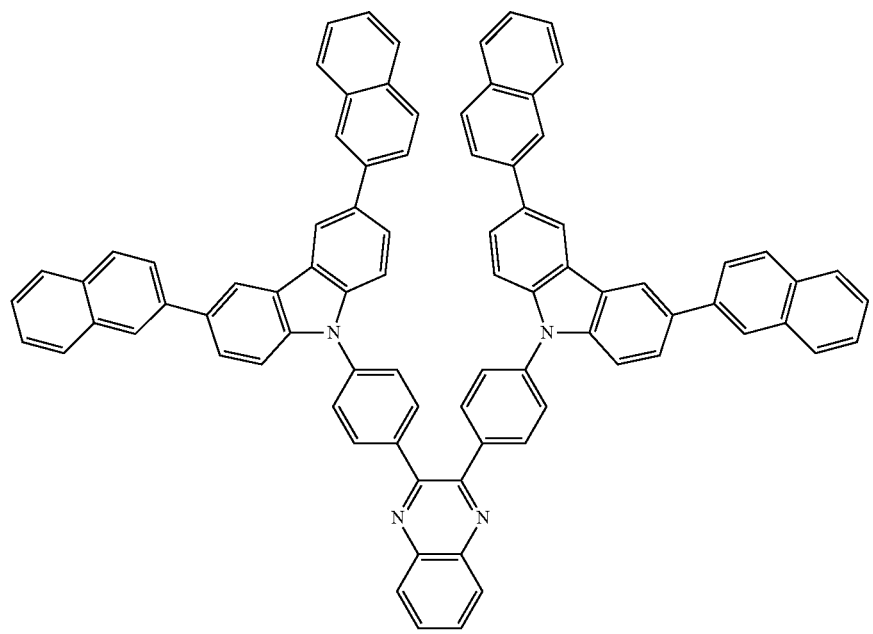
(26)
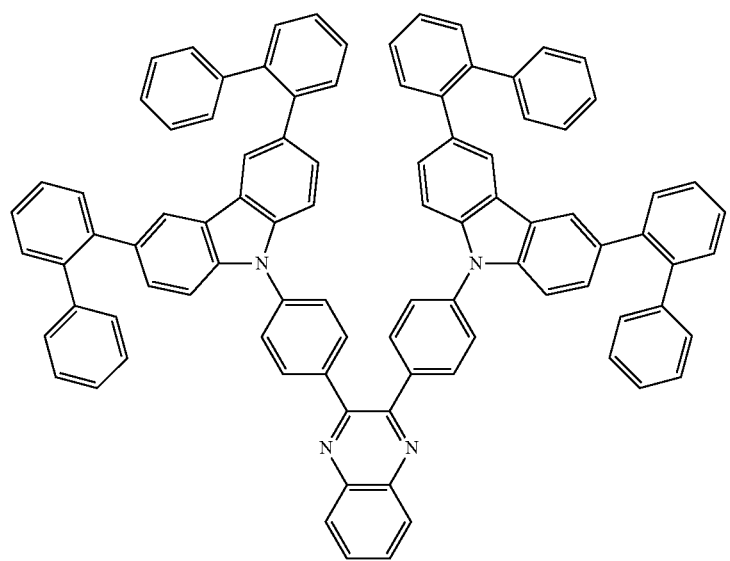

(27)
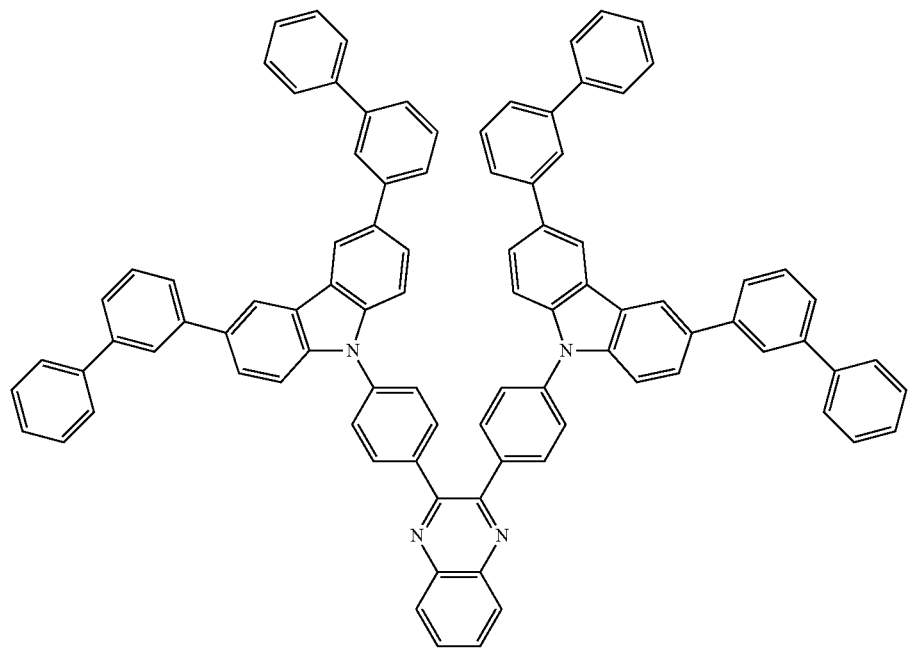
(28)
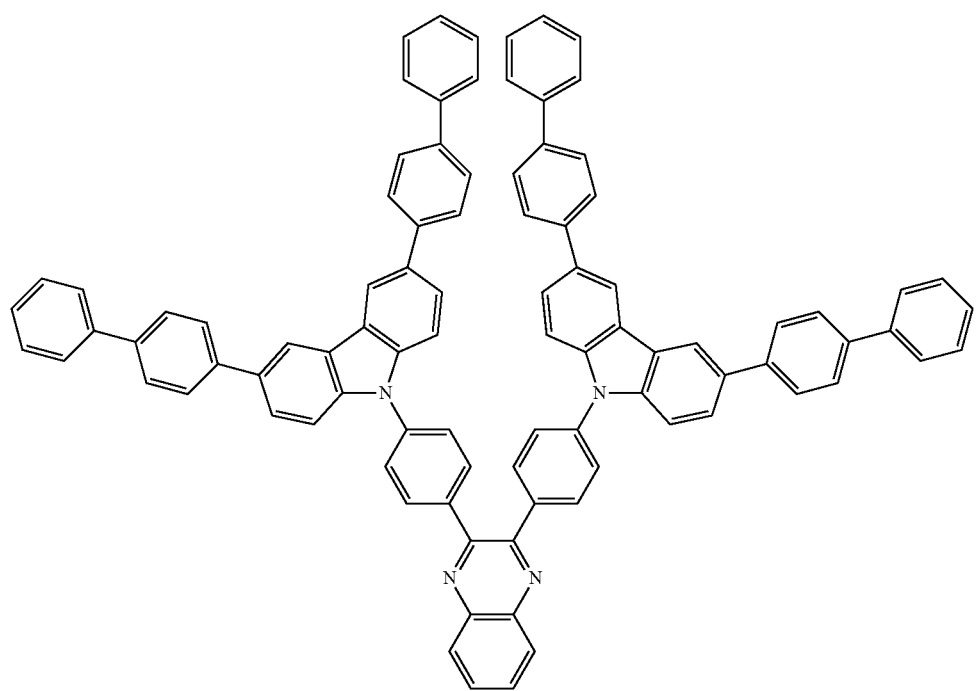

(29)
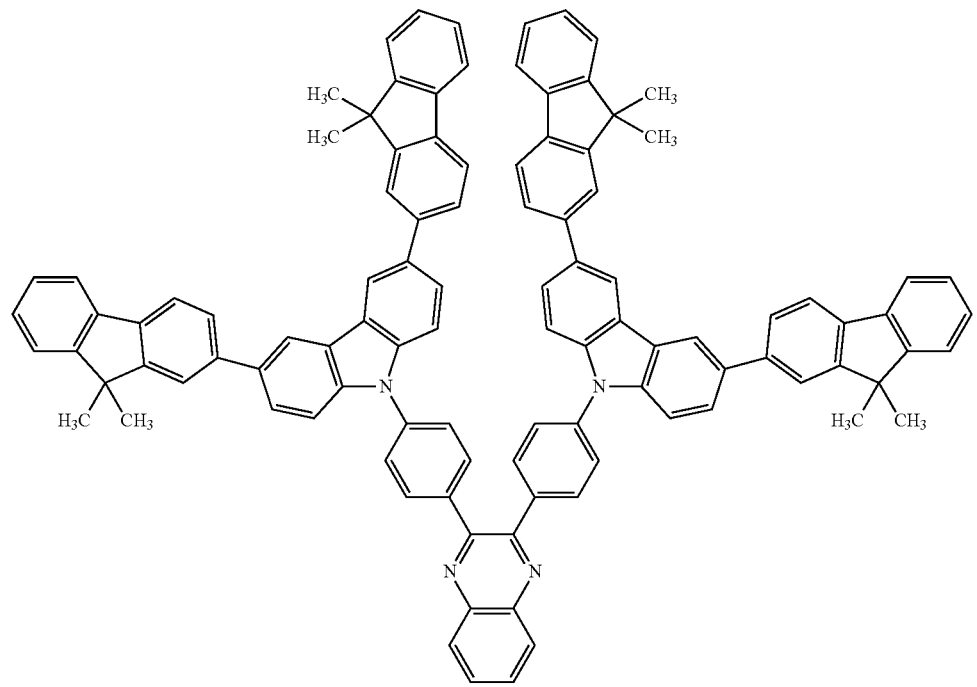
(30)
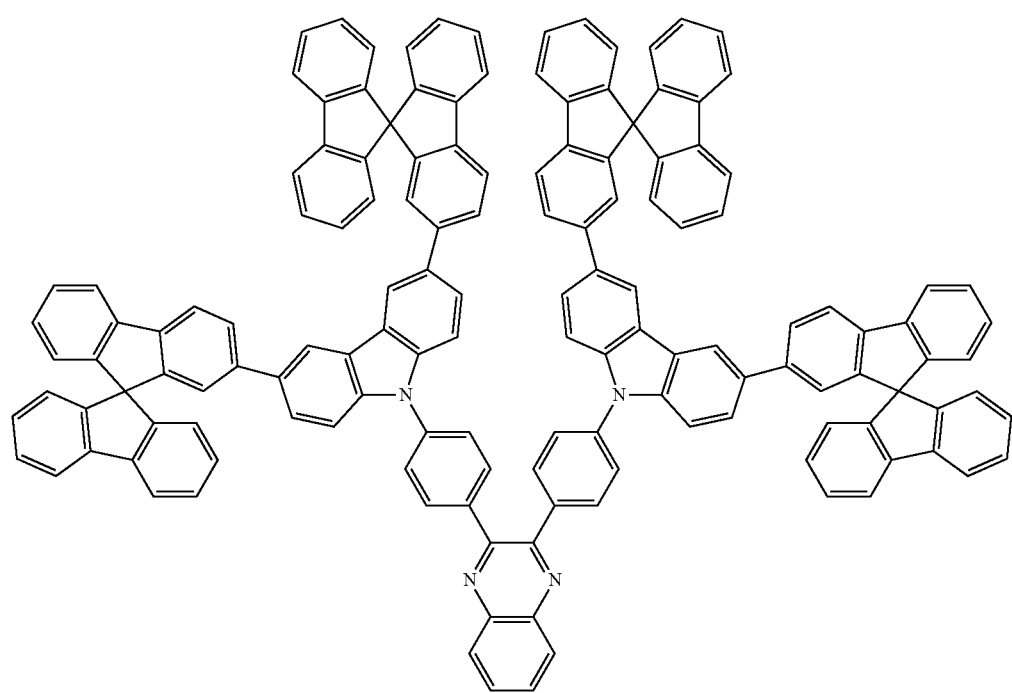

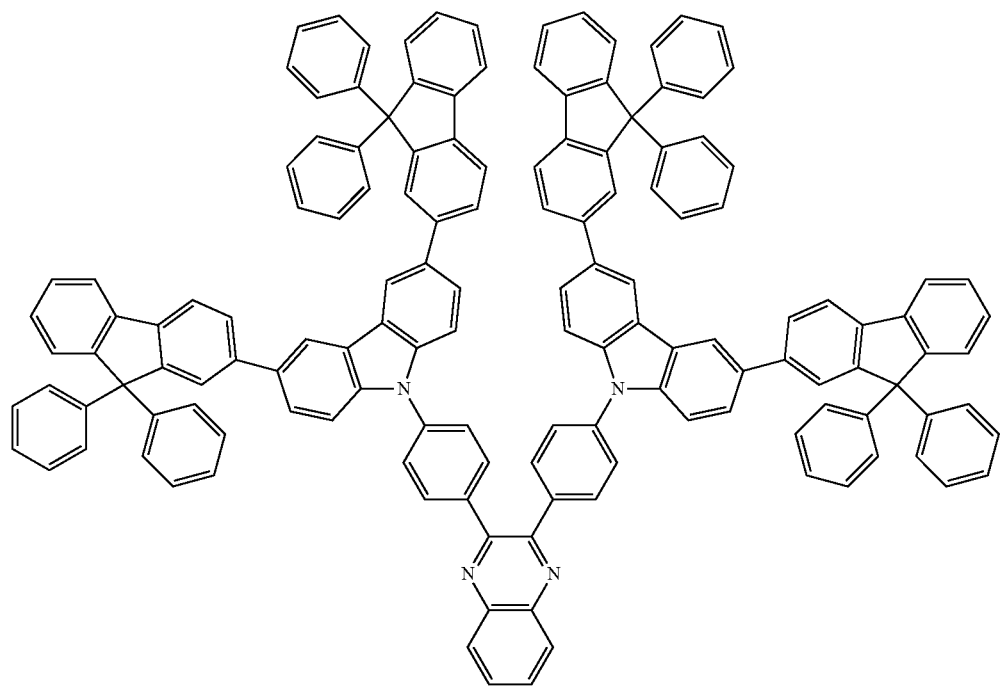
(31)
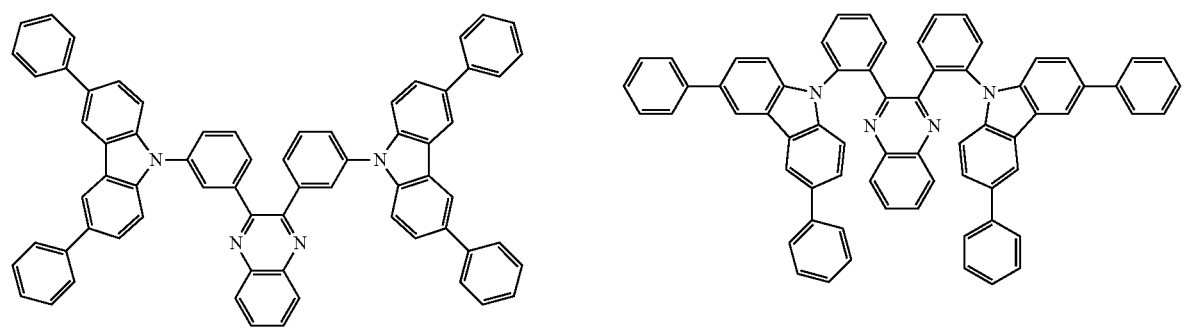
(32)            (33)
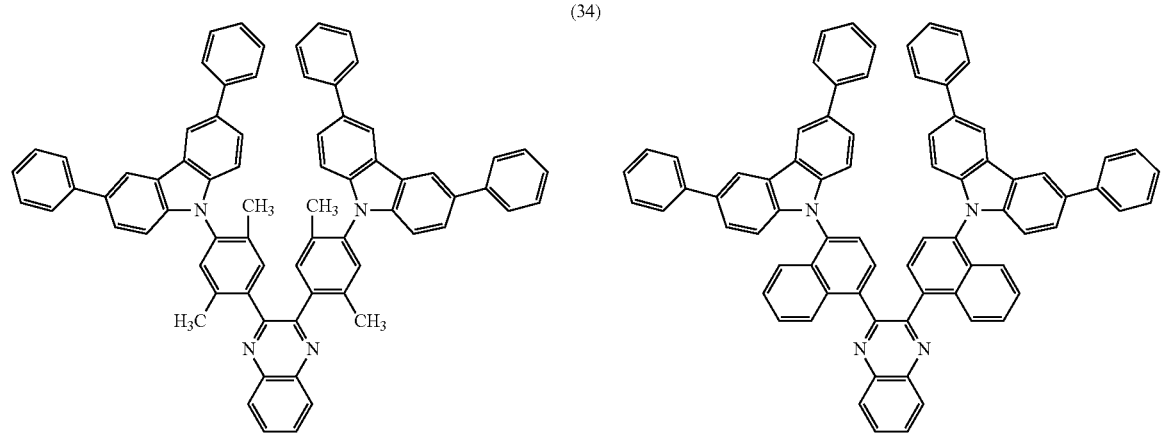
(34)            (35)

(36)
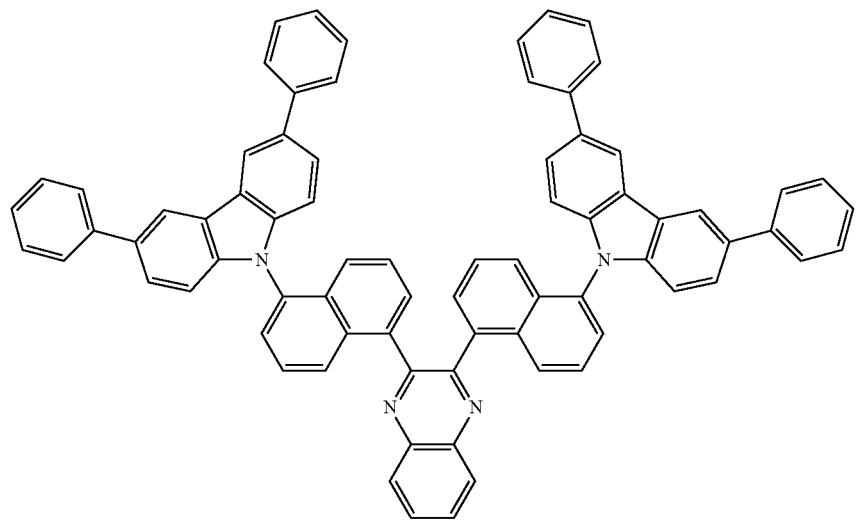
(37)
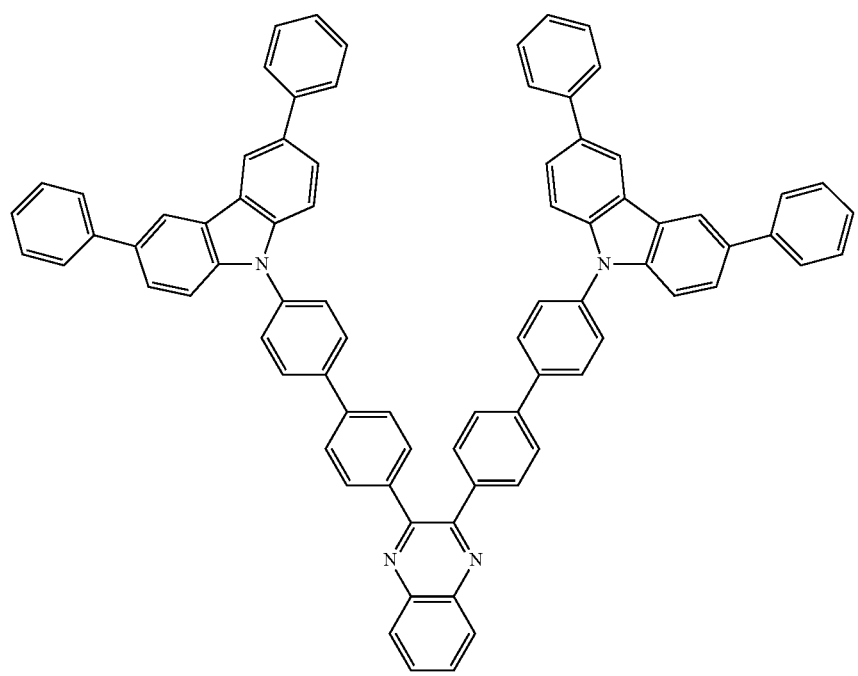

(38)
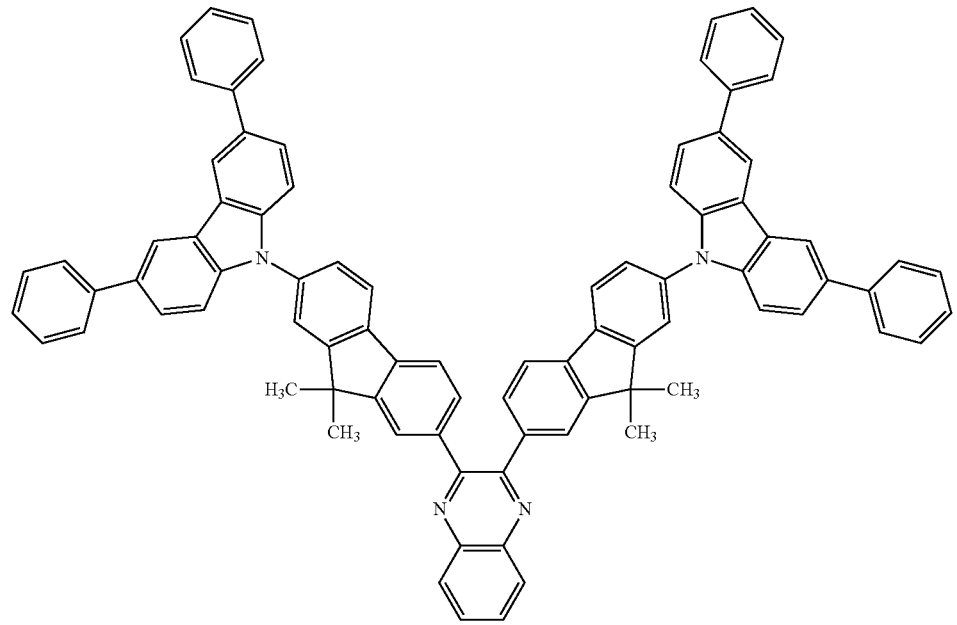
(39)
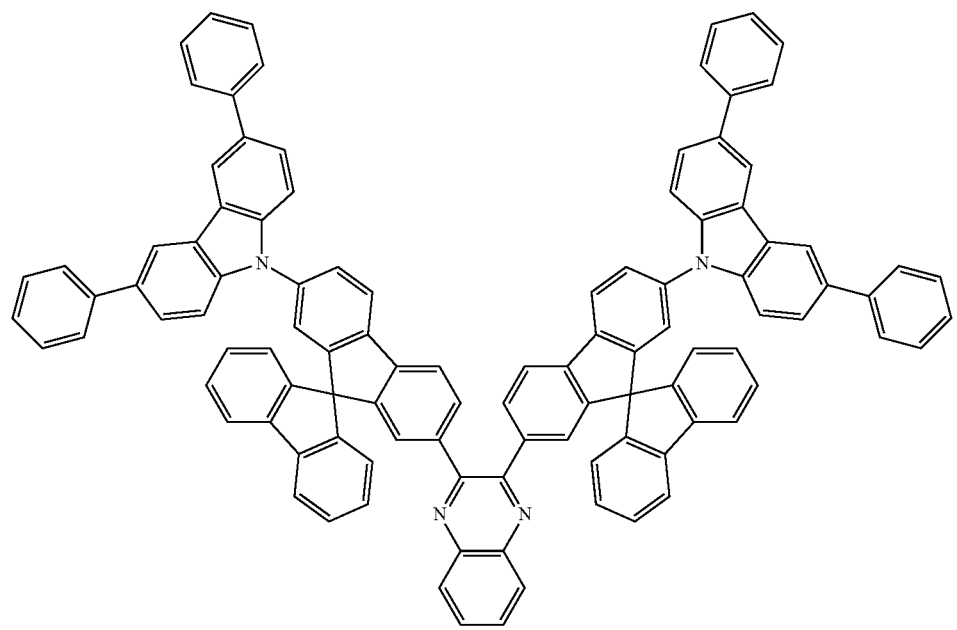

(40)

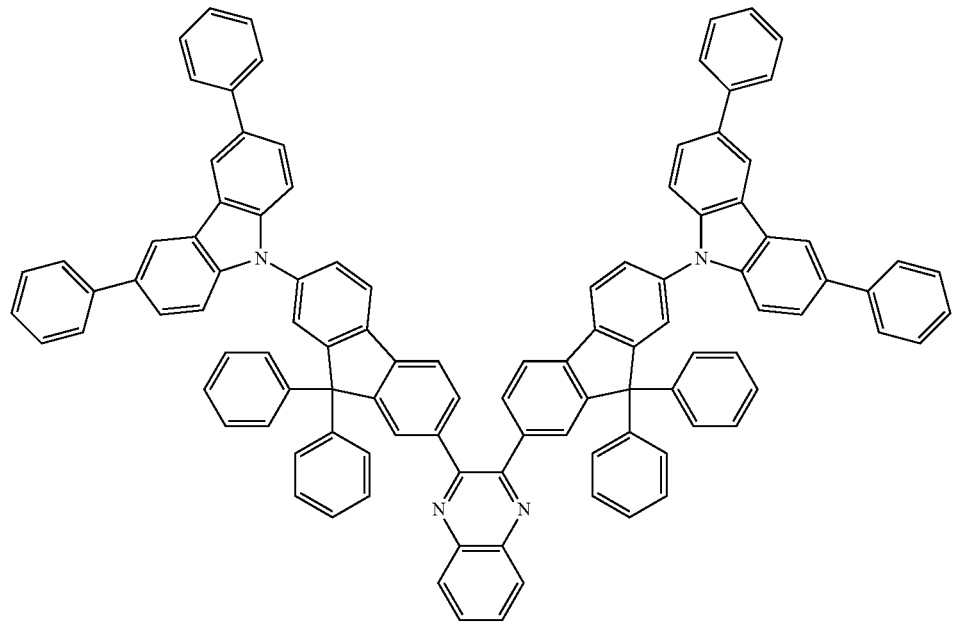

As a synthesis method of quinoxaline derivatives of the present invention, various kinds of reactions can be applied. For example, quinoxaline derivatives of the present invention can be manufactured by synthesis reactions represented by the following reaction schemes (A-1) and (A-2).

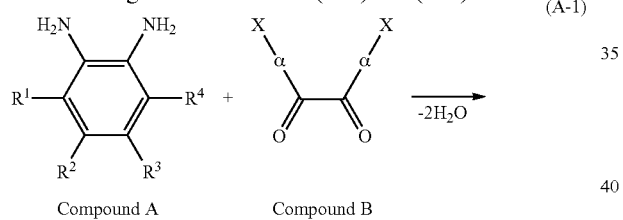

(A-1)

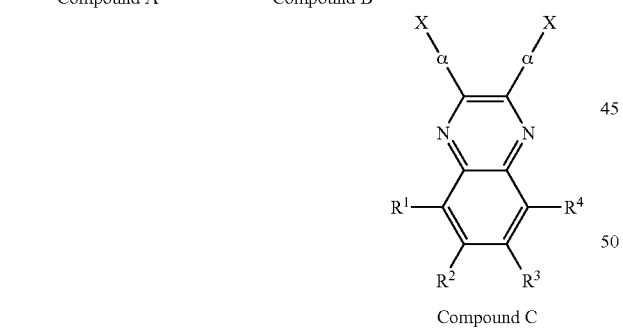

(A-2)

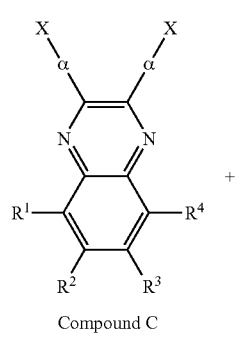

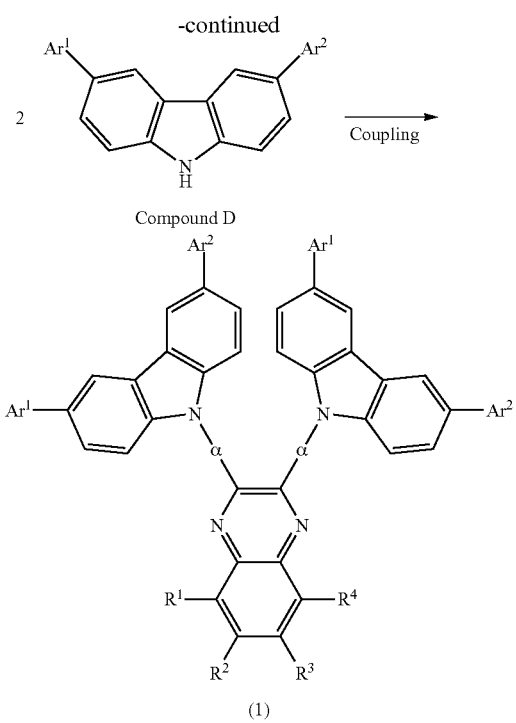

A compound (Compound C) is formed, and the compound C has a quinoxaline skeleton formed by a condensation reaction of a diketone derivative (Compound B) in which an aryl group α is substituted by a halogen atom X, and 1,2-diaminobenzene derivative (compound A). The halogen atom can be bromine, iodine, or chlorine, but bromine is preferable in consideration of easy handling and moderate reactivity.

The obtained halogen-substituted quinoxaline derivative (Compound C) is coupled with two equivalent 3,6-diarylcarbazole (Compound D) in the presence of a base by using a metallic catalyst to obtain a quinoxaline derivative of the present invention represented by the general formula (1). As the metallic catalyst for the coupling, a palladium catalyst such as palladium(II) acetate, tetrakis(triphenylphosphine)palladium(0), or bis(dibenzylideneacetone)palladium(0), monovalent copper such as copper(I) iodide or the like can be used. As a base, for example, an inorganic base such as potassium carbonate or sodium carbonate or an organic base such as metal alkoxide can be used.

3,6-diarylcarbazole derivative in the above scheme can be synthesized by the following scheme, for example.

When $Ar^2$ is the same as $Ar^1$, as shown in the following synthesis scheme (B-1), carbazole whose third or sixth position is halogen-substituted is coupled with two equivalent arylboronic acid or an aryl organoboron compound in the presence of a base by using a palladium catalyst or a nickel catalyst, and thus an objective 3,6-diarylcarbazole can be obtained. $R^{21}$ and $R^{22}$ each represent a hydrogen atom or an alkyl group having 1 to 10 carbon atoms, and $R^{21}$ and $R^{22}$ may be bound to each other to faun a ring. As a base, for example, an inorganic base such as potassium carbonate or sodium carbonate or an organic base such as metal alkoxide can be used. As the palladium catalyst, palladium(II) acetate, tetrakis(triphenylphosphine)palladium(0), bis(dibenzylideneacetone)palladium(0), or the like can be used.

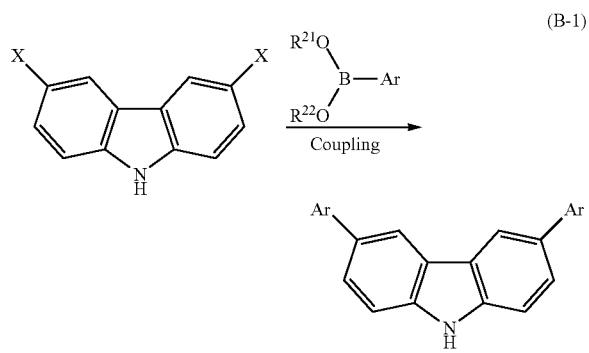

(B-1)

A quinoxaline derivative of the present invention can have excellent heat resistance as a result of introduction of an aryl group into the third and sixth positions of carbazole. Thus, by using a quinoxaline derivative of the present invention for an electronic device, the electronic device can also have excellent heat resistance.

Embodiment Mode 2

A mode of a light-emitting element using a quinoxaline derivative of the present invention will be hereinafter described with reference to FIG. 1A.

A light-emitting element of the present invention has a plurality of layers between a pair of electrodes. The plurality of layers are formed by stacking a layer containing a substance with a high carrier-injecting property and a layer containing a substance with a high carrier-transporting property so that a light-emitting region is formed apart from the electrodes, i.e., so that carrier recombination is carried out in a portion apart from the electrodes.

In this embodiment mode, the light-emitting element includes a first electrode 102, an EL layer 108, and a second electrode 107, which are stacked in this order. The EL layer 108 includes a first layer 103, a second layer 104, a third layer 105, and a fourth layer 106 which are stacked in sequence. In the explanation of this embodiment mode, the first electrode 102 functions as an anode and the second electrode 107 functions as a cathode.

The substrate 101 is used as a support for the light-emitting element. As the substrate 101, for example, a glass substrate, a plastic substrate, or the like can be used. Other substrates than these can also be used as long as they can function as a support during a manufacturing process of the light-emitting element.

The first electrode 102 is preferably formed of a metal, alloy, conductive compound, mixture of these, or the like each having a high work function (specifically, 4.0 eV or higher). Specifically, as examples, indium tin oxide (ITO), indium tin oxide including silicon, indium zinc oxide (IZO) which is indium oxide contains zinc oxide (ZnO) at 2 to 20 wt %, indium oxide which contains tungsten oxide at 0.5 to 5 wt % and zinc oxide at 0.1 to 1 wt %, and the like are given. Films of these conductive metal oxides are usually fanned by sputtering; however, a sol-gel method or the like may also be used. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), or the like is given.

The first layer 103 includes a substance with a high hole-injecting property and can be faulted of molybdenum oxide, vanadium oxide, ruthenium oxide, tungsten oxide, manganese oxide, or the like. In addition, phthalocyanine (abbreviation: $H_2PC$), a phthalocyanine-based compound such as copper phthalocyanine (CuPC), a high-molecular material such as poly(ethylenedioxythiophene)/poly(styrenesulfonate) (PEDOT/PSS), or the like can also be used to form the first layer 103.

Moreover, the first layer 103 can be formed of a composite material including an organic compound and an inorganic compound. In particular, in a composite material including an organic compound and an inorganic compound exhibiting an electron-accepting property to the organic compound, electrons are transported between the organic compound and the inorganic compound to increase carrier density; thus, the hole-injecting property and the hole-transporting property are excellent.

When the first layer 103 is formed of a composite material including an organic compound and an inorganic compound, since ohmic contact with the first electrode 102 becomes possible, the material for the first electrode can be selected regardless of its work function.

The inorganic compound used for the composite material is preferably an oxide of a transition metal. Moreover, an oxide of a metal belonging to any of Groups 4 to 8 in the periodic table can be used. Specifically, vanadium oxide, niobium oxide, tantalum oxide, chromium oxide, molybdenum oxide, tungsten oxide, manganese oxide, and rhenium oxide are preferable since they have high electron-accepting properties. Above all, molybdenum oxide is preferable because it is stable in the air, it has a low moisture-absorption property, and it is easily handled.

The organic compound used for the composite material can be various kinds of compounds including an aromatic amine compound, a carbazole derivative, aromatic hydrocarbon, a high-molecular compound (such as polymer), and so on. The organic compound used for the composite material preferably has a high hole-transporting property. Specifically, a substance having a hole mobility of $10^{-6}$ $cm^2/Vs$ or higher is preferable. However, other materials than these can also be used, as long as they have hole-transporting properties higher than electron-transporting properties. Specifically, the organic compound which can be used for the composite material will hereinafter be described below.

For example, the aromatic amine compound may be N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N-(3-methylphenyl)-N-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); or the like.

As the carbazole derivative which can be used for the composite material, specifically, the following can be given: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); or the like.

Moreover, 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl-2,3,5,6-tetraphenylbenzene; or the like can be used.

As the aromatic hydrocarbon which can be used for the composite material, for example, the following can be given: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; or the like. In addition to these, pentacene, coronene, or the like can also be used. In this way, the aromatic hydrocarbon having a hole mobility of $1\times10^{-6}$ cm$^2$/Vs or higher and 14 to 42 carbon atoms, is more preferably used.

The aromatic hydrocarbon which can be used for the composite material may have a vinyl skeleton. As the aromatic hydrocarbon having a vinyl group, for example, 4,4'-bis(2,2-diphenylvinyl)biphenyl (abbreviation: DPVBi); 9,10-bis[4-(2,2-diphenylvinyl)phenyl]anthracene (abbreviation: DPVPA); or the like is given.

In addition, a high-molecular compound such as poly(N-vinylcarbazole) (abbreviation: PVK) or poly(4-vinyltriphenylamine) (abbreviation: PVTPA) can be used.

As a substance forming the second layer 104, a substance having a high hole-transporting property, specifically, an aromatic amine compound (that is, a compound having a benzene ring-nitrogen bond) is preferable. As a material that is widely used, 4,4'-bis[N-(3-methylphenyl)-N-phenylamino]biphenyl, derivatives thereof such as 4,4'-bis[N-(1-napthyl)-N-phenylamino]biphenyl (hereinafter referred to as NPB), and star burst aromatic amine compounds such as 4,4',4"-tris(N,N-diphenyl-amino)triphenylamine, and 4,4',4"-tris[N-(3-methylphenyl)-N-phenylamino]triphenylamine can be given. These materials described here mainly are substances each having a hole mobility of greater than or equal to $10^{-6}$ cm$^2$/Vs. However, other materials than these compounds may also be used as long as the hole transporting properties thereof are higher than the electron transporting properties. The second layer 104 is not limited to a single layer, and a mixed layer of the aforementioned substances, or a stacked layer which comprises two or more layers each including the aforementioned substance may be used.

The third layer 105 is a layer containing a substance with a light-emitting property (also referred to as a light-emitting substance). In this embodiment mode, the third layer 105 includes a quinoxaline derivative of the present invention described in Embodiment Mode 1. A quinoxaline derivative of the present invention exhibits light emission of blue to blue green, and thus, it can be preferably used as a light-emitting substance for a light-emitting element.

The fourth layer 106 can be formed of a substance with a high electron-transporting property. For example, the fourth layer 106 includes the following metal complex having a quinoline skeleton or a benzoquinoline skeleton, or the like: tris(8-quinolinolato)aluminum (abbreviation: Alq); tris(4-methyl-8-quinolinolato)aluminum (abbreviation: Almq$_3$); bis(10-hydroxybenzo[h]-quinolinato)beryllium (abbreviation: BeBq$_2$); bis(2-methyl-8-quinolinolato)-4-phenylphenolato-aluminum (abbreviation: BAlq); and the like. Besides those, the following metal complexes having an oxazole-based ligand or a thiazole-based ligand, or the like can be used: bis[2-(2-hydroxyphenyl)benzoxazolato]zinc (abbreviation: Zn(BOX)$_2$); bis[2-(2-hydroxyphenyl)benzothiazolato]zinc (abbreviation: Zn(BTZ)$_2$); and the like. Furthermore, in addition to the metal complexes, 2-(4-biphenylyl)-5-(4-tert-butylphenyl)-1,3,4-oxadiazole (abbreviation: PBD); 1,3-bis[5-(p-tert-butylphenyl)-1,3,4-oxadiazol-2-yl]benzene (abbreviation: OXD-7); 3-(4-tert-butylphenyl)-4-phenyl-5-(4-biphenylyl)-1,2,4-triazole (abbreviation: TAZ); 3-(4-tert-butylphenyl)-4-(4-ethylphenyl)-5-(4-biphenylyl)-1,2,4-triazole (abbreviation: p-EtTAZ); bathophenanthroline (abbreviation: BPhen); bathocuproin (abbreviation: BCP); and the like can also be used. The substances mentioned here mainly have an electron mobility of $10^{-6}$ cm$^2$/Vs or higher. It is to be noted that the fourth layer 106 may include a substance other than those above as long as the substance has a higher electron-transporting property than hole-transporting property. Moreover, the fourth layer 106 may have not only a single-layer structure but also a stacked-layer structure including two or more layers formed of the above-mentioned substances.

The second electrode 107 can be formed of a metal, alloy, electrically conductive compound, or mixture of these, each having a low work function (specifically, 3.8 eV or lower). As a typical example of a cathode material, an element belonging to Group 1 or 2 in the periodic table, i.e., an alkali metal such as lithium (Li) or cesium (Cs), or an alkaline-earth metal such as magnesium (Mg), calcium (Ca), or strontium (Sr); an alloy containing any of these (such as MgAg or AlLi); a rare earth metal such as europium (Er) or ytterbium (Yb); an alloy containing a rare earth metal; or the like can be used. However, when a layer having a function of promoting electron injection is provided between the second electrode 107 and the light-emitting layer as a stack with the second electrode, the second electrode 107 can be formed of any of various conductive materials such as Al, Ag, ITO, or ITO including silicon regardless of its work function.

For the layer having a function of promoting electron injection, a compound of an alkali metal or an alkaline-earth metal, such as lithium fluoride (LiF), cesium fluoride (CsF), or calcium fluoride (CaF$_2$) can be used. Further, a layer including an electron-transporting substance which contains an alkali metal, an alkaline-earth metal, an alkali metal compound, or an alkaline-earth metal compound, for example, Alq mixed with lithium oxide and magnesium nitride, magnesium (Mg), or lithium (Li) may be used.

The first layer 103, the second layer 104, the third layer 105, and the fourth layer 106 can be formed by not only an evaporation method but also various methods such as an ink jet method or a spin coating method. Moreover, a different film-formation method may be used for each electrode or each layer.

In the light-emitting element of the present invention having the aforementioned structure, current flows by a potential difference generated between the first electrode 102 and the second electrode 107 and holes and electrons are recombined in the third layer 105, which is the layer containing a substance with a high light-emitting property; thus, light is emitted. In other words, in this structure, a light-emitting region is formed in the third layer 105.

Figure 1B:
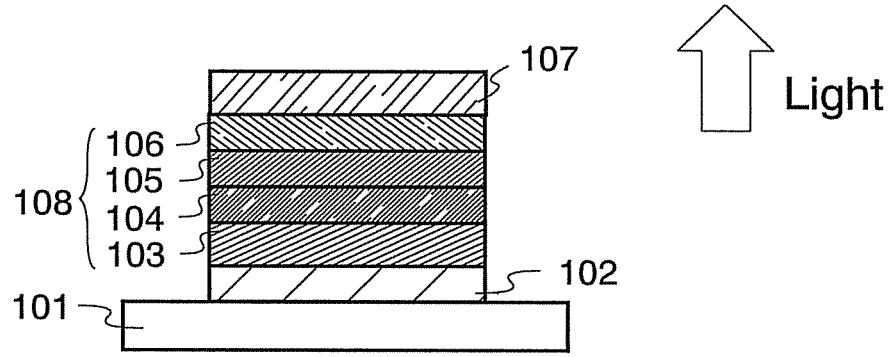
Figure 1C:
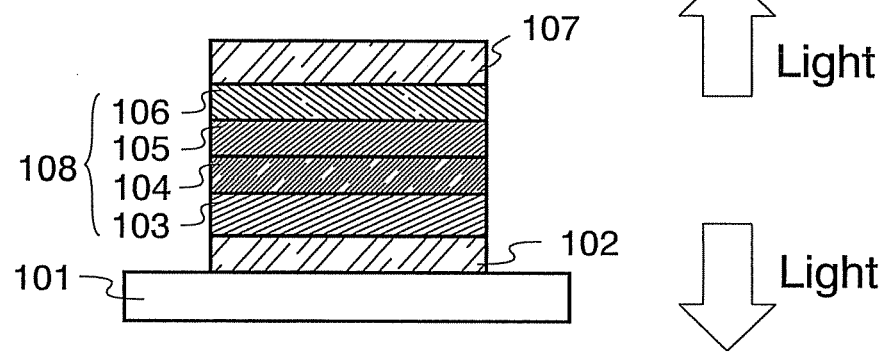

The emitted light is extracted to the outside through one or both of the first electrode 102 and the second electrode 107. Therefore, one or both of the first electrode 102 and the second electrode 107 is/are an electrode with a light-transmitting property. When only the first electrode 102 is an electrode with a light-transmitting property, the emitted light is extracted from the substrate side through the first electrode 102 as shown in FIG. 1A. Meanwhile, when only the second electrode 107 is an electrode with a light-transmitting property, the emitted light is extracted from the side opposite to the substrate side through the second electrode 107 as shown in FIG. 1B. When each of the first electrode 102 and the second electrode 107 is formed of a substance with a light-transmitting property, the emitted light is extracted from both the substrate side and the side opposite to the substrate side through the first electrode 102 and the second electrode 107 as shown in FIG. 1C.

The structure of the layers provided between the first electrode 102 and the second electrode 107 is not limited to the aforementioned one. A structure other than the aforementioned one may also be used as long as a light-emitting region in which holes and electrons are recombined is provided in a portion apart from the first electrode 102 and the second electrode 107 so that light extinction caused by approximation of the light-emitting region to metal is suppressed.

That is to say, the stacked-layer structure is not particularly limited, and layers containing a substance with a high electron-transporting property, a substance with a high hole-transporting property, a substance with a high electron-injecting property, a substance with a high hole-injecting property, a substance with a bipolar property (a material with a high electron and hole transporting property), a substance with a hole-blocking property, and the like may be freely combined with a quinoxaline derivative of the present invention.

Figure 2:
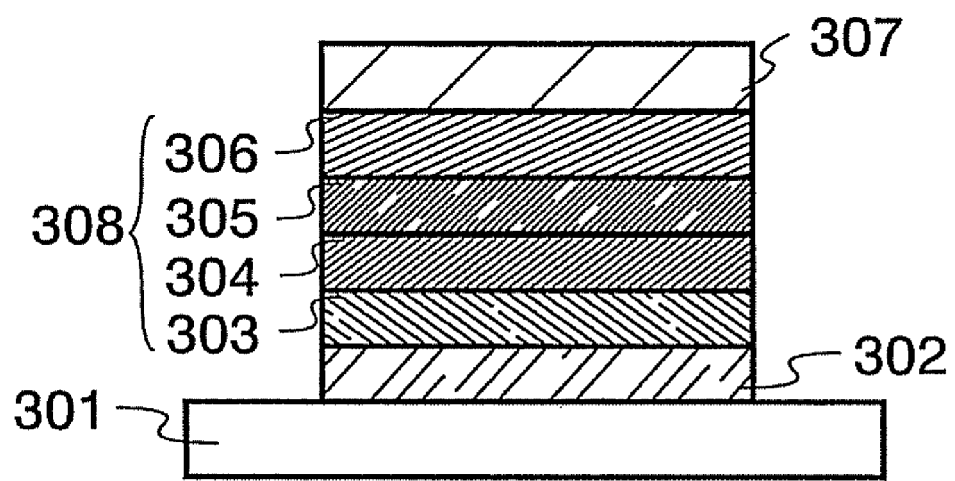
FIG. 2 illustrates a light-emitting element of the present invention.

In the light-emitting element shown in FIG. 2, a first electrode 302 serving as a cathode, an EL layer 308 and a second electrode 307 serving as an anode are stacked in sequence. The EL layer 308 includes a first layer 303 formed of a highly electron transporting substance, a second layer 304 including a light-emitting substance, a third layer 305 formed of a high hole-transporting substance, and a fourth layer 306 formed of a high hole-injecting property which are stacked in sequence from the first electrode 302 side. It is to be noted that reference numeral 301 denotes a substrate.

In this embodiment mode, the light-emitting element is manufactured over a substrate made of glass, plastic, or the like. When a plurality of such light-emitting elements are manufactured over one substrate, a passive matrix light-emitting device can be manufactured. Moreover, for example, thin film transistors (TFTs) may be formed over a substrate made of glass, plastic, or the like so that light-emitting elements are manufactured over electrodes electrically connected to the TFTs. Thus, an active matrix light-emitting device in which driving of the light-emitting elements is controlled by the TFTs can be manufactured. The structure of such TFTs is not particularly limited. The TFTs may be either a staggered type or an inverted staggered type. The crystallinity of a semiconductor used for the TFTs is not limited in particular, and the semiconductor may be either amorphous or crystalline. Moreover, a driver circuit formed on the TFT array substrate may include N-type and P-type TFTs or only one of N-type and P type TFTs.

Since a quinoxaline derivative of the present invention has a light-emitting property, it can be used as a light-emitting layer by itself as shown in this embodiment mode, without containing another light-emitting substance.

In addition, a quinoxaline derivative of the present invention includes almost no microcrystal components in forming a film, and a formed film using the quinoxaline derivative also has almost no microcrystal components, so that the film can have an amorphous state. In other words, an excellent film quality can be obtained, and thus a favorable light-emitting element having almost no defects such as dielectric breakdown due to electric field concentration can be manufactured.

Furthermore, since a quinoxaline derivative of the present invention has excellent heat resistance, a light-emitting element having excellent heat resistance can be formed using the quinoxaline derivative of the present invention.

Embodiment Mode 3

Embodiment Mode 3 will explain a light-emitting element with a structure different from the structure shown in Embodiment Mode 2.

The third layer 105 described in Embodiment Mode 2 includes a quinoxaline derivative of the present invention which is dispersed in another substance, so that the quinoxaline derivative of the present invention can emit light. The quinoxaline derivative of the present invention emits light of blue to blue green, and thus, a light-emitting element emitting light of blue to blue green can be provided.

As the substance in which a quinoxaline derivative of the present invention is dispersed, various materials such as the following can be used, in addition to the substance with a high hole-transporting property and the substance with a high electron-transporting property described in Embodiment Mode 2. For example, 4,4'-di(N-carbazolyl)biphenyl (abbreviation: CBP), 2,2',2''-(1,3,5-benzenetriyl)tris(1-phenyl-1H-benzimidazole) (abbreviation: TPBI) 9,10-di(2-naphthyl)anthracene (abbreviation: DNA), 2-tert-butyl-9,10-di(2-naphthyl)anthracene (abbreviation: t-BuDNA), and the like are given.

Since the quinoxaline derivative of the present invention has high excellent heat resistance, a light-emitting element with the use of the quinoxaline derivative of the present invention can have excellent heat resistance.

The structures described in Embodiment Mode 2 can be applied to the other elements than the third layer 105.

Embodiment Mode 4

Embodiment Mode 4 will explain a light-emitting element having a structure different from those described in Embodiment Modes 2 and 3.

The third layer 105 described in Embodiment Mode 2 includes a light-emitting substance in which a quinoxaline derivative of the present invention is dispersed, so that the light-emitting substance of the present invention can emit light.

Since a quinoxaline derivative of the present invention has almost no microcrystal components contained in film formation and has excellent film quality, it can be preferably used as a material for dispersing another light-emitting substance.

When a quinoxaline derivative of the present invention is used as a material for dispersing another light-emitting substance, the emission color of the light-emitting substance can be observed. A mixed color of the emission color of the quinoxaline derivative of the present invention and the emission color of the light-emitting substance dispersed in the quinoxaline derivative can be observed.

As a light-emitting substance dispersed in a quinoxaline derivative of the present invention, various material can be used. Specifically, fluorescence emitting substances such as 4-(dicyanomethylene)-2-methyl-6-(p-dimethylaminostyryl)-4H-pyran (abbreviation: DCM1), 4-(dicyanomethylene)-2-methyl-6-(julolidin-4-yl-vinyl)-4H-pyran (abbreviation: DCM2), N,N-dimethylquinacridon (abbreviation: DMQd), 9,10-diphenylanthracene (abbreviation: DPA), 5,12-diphenyltetracene (abbreviation: DPT), coumarin 6, perylene, or rubrene can be used, and additionally, phosphorescence emitting substances such as bis(2-(2'-benzothienyl)pyridinato-N,C3')(acetylacetonato)iridium (abbreviation: Ir(btp)$_2$(acac)), or (acetylacetonato)bis[2,3-bis(4-fluorophenyl)quinoxalinato]iridium(III) (abbreviation: Ir(Fdpq)$_2$(acac)) can be employed, too.

As a light-emitting substance dispersed in a quinoxaline derivative of the present invention, a red phosphorescence emitting compound such as Ir(btp)$_2$(acac) or Ir(Fdpq)$_2$(acac) described above, which has a peak of the emission spectrum within the range of 560 nm to 700 nm is preferably used. Accordingly, a red light-emitting element having excellent heat resistance and emission efficiency can be provided.

Since the quinoxaline derivative of the present invention has excellent heat resistance, a light-emitting element with the use of the quinoxaline derivative of the present invention can have excellent heat resistance.

The structures described in Embodiment Mode 2 can be applied to the other elements than the third layer 105.

Embodiment Mode 5

Embodiment Mode 5 will describe a mode of a light-emitting element in which a plurality of light-emitting units of the present invention are stacked (hereinafter this light-emitting element is referred to as a stacked-type element) with reference to FIG. 3. The light-emitting element includes a plurality of light-emitting units between a first electrode and a second electrode.

Figure 3:
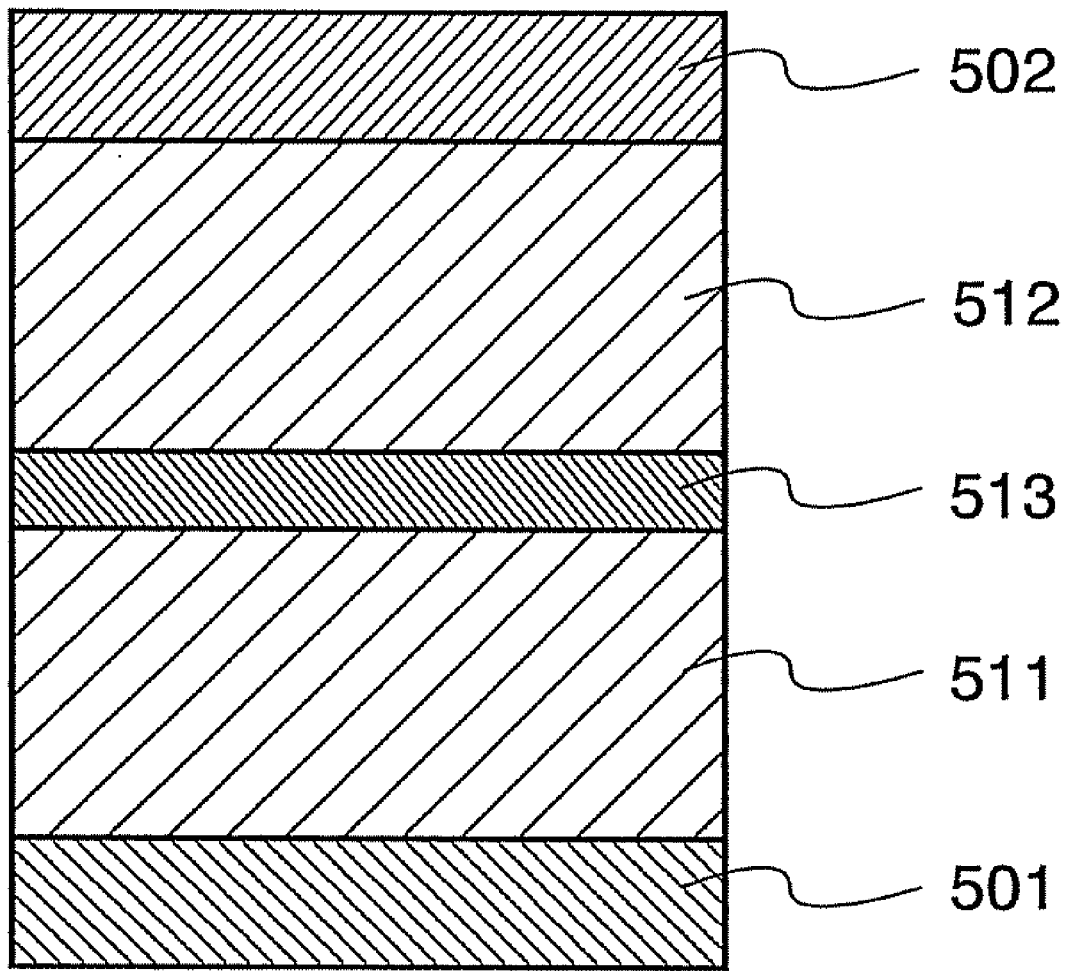
FIG. 3 illustrates a light-emitting element of the present invention.

In FIG. 3, a first light-emitting unit 511 and a second light-emitting unit 512 are stacked between a first electrode 501 and a second electrode 502. The first electrode 501 and the second electrode 502 may be similar to those shown in Embodiment Mode 2. The first light-emitting unit 511 and the second light-emitting unit 512 may have either the same structure or a different structure, at least one of the units includes a quinoxaline derivative of the present invention, and the structure may be similar to the structure of the EL layers described in Embodiment Modes 2 to 4.

A charge-generating layer 513 includes a composite material of an organic compound and a metal oxide. The composite material of an organic compound and a metal oxide includes the composite material shown in Embodiment Mode 2 and a metal oxide such as vanadium oxide, molybdenum oxide, or tungsten oxide. As the organic compound, various compounds such as an aromatic amine compound, a carbazole derivative, aromatic hydrocarbon, and a high molecular compound (polymer, or the like) can be used. As the organic compound, it is preferable to use the organic compound which has a hole-transporting property and has a hole mobility of 10$^{-6}$ cm$^2$/Vs or higher. However, other substances than these may also be used as long as they have hole-transporting properties higher than the electron-transporting properties.

The composite material of the organic compound and the metal oxide can achieve low-voltage driving and low-current driving because the composite material has a superior carrier-injecting property and a carrier-transporting property.

Alternatively, the charge-generating layer 513 may be formed by combining the composite material of the organic compound and the metal oxide with another material. For example, a layer containing the composite material of the organic compound and the metal oxide may be combined with a layer containing a compound of a substance selected from substances with an electron-donating property and a compound with a high electron-transporting property. Moreover, a layer containing the composite material of the organic compound and the metal oxide may be combined with a transparent conductive film.

In any case, the charge-generating layer 513 interposed between the first light-emitting unit 511 and the second light-emitting unit 512 may inject electrons to one of these light-emitting units and holes to the other when voltage is applied to the first electrode 501 and the second electrode 502.

Although this embodiment mode describes the light-emitting element having two light-emitting units, the present invention can be similarly applied to a light-emitting element in which three or more light-emitting units are stacked. When the charge-generating layer is provided between the pair of electrodes so as to partition the plural light-emitting units like the light-emitting element of this embodiment mode, the element can have long lifetime in a high luminous region while keeping low current density. When the light-emitting element is applied for illumination, voltage drop due to resistance of an electrode material can be reduced, thereby achieving homogeneous light emission in a large area. Moreover, a light-emitting device of low power consumption, which can be driven at low voltage, can be achieved.

This embodiment mode can be freely combined with any of the other embodiment modes.

Embodiment Mode 6

Embodiment Mode 7 will explain a light-emitting device manufactured by using a quinoxaline derivative of the present invention.

In this embodiment mode, a light-emitting device manufactured by using a quinoxaline derivative of the present invention is explained with reference to FIGS. 4A and 4B. FIG. 4A is a top view of the light-emitting device, while FIG. 4B is a cross-sectional view along a line A-A' and a line B-B' in FIG. 4A. This light-emitting device includes a driver circuit portion (source side driver circuit) 601, a pixel portion 602, and a driver circuit portion (gate side driver circuit) 603 in order to control the light emission of the light-emitting element. Moreover, reference numeral 604 denotes a sealing substrate; 605, a sealant; and 607, a space surrounded by the sealant 605.

A lead wiring 608 transmits signals to be inputted to the source side driver circuit 601 and the gate side driver circuit 603 and receive a video signal, a clock signal, a start signal, a reset signal, and the like from an FPC (Flexible Printed Circuit) 609 which is an external input terminal. Although only an FPC is shown here, this FPC may have a printed wiring board (PWB) attached. In this specification, the light-emitting device includes not only a light-emitting device alone but also a light-emitting device with an FPC or a PWB attached thereto.

Next, the cross-sectional structure is explained with reference to FIG. 4B. Although the driver circuit portion and the pixel portion are formed over an element substrate 610, the source side driver circuit 601 as the driver circuit portion and one pixel in the pixel portion 602 are shown here.

In the source side driver circuit 601, a CMOS circuit in which an n-channel TFT 623 and a p-channel TFT 624 are combined is formed. The driver circuit may be formed by various CMOS circuits, PMOS circuits, or NMOS circuits. Although this embodiment mode describes a driver-integrated type in which the driver circuit is formed over the substrate, the structure may be different. For example, the driver circuit may be formed not over the substrate but outside the substrate.

Moreover, the pixel portion 602 is fanned with a plurality of pixels including a switching TFT 611, a current controlling TFT 612, and a first electrode 613 electrically connected to a drain of the current controlling TFT 612. An insulator 614 is formed covering an end portion of the first electrode 613. Here, the insulator 614 is formed using a positive photosensitive acrylic resin film.

In order to have favorable coverage, the insulator 614 is formed so as to have a curved surface with curvature at its upper end or lower end portion. For example, in a case of using a positive photosensitive acrylic for the insulator 614, only the upper end portion of the insulator 614 preferably has a curved surface with a radius of curvature (0.2 to 3 μm). As the insulator 614, either a negative type which becomes insoluble in etchant by light irradiation or a positive type which becomes soluble in etchant by light irradiation can be used.

An EL layer 616 and a second electrode 617 are formed over the first electrode 613. Here, the first electrode 613 functioning as an anode is preferably formed of a material with a high work function. For example, a single-layer film of an ITO film, an indium tin oxide film including silicon, an indium oxide film containing 2 to 20 wt % of zinc oxide, a titanium nitride film, a chromium film, a tungsten film, a Zn film, a Pt film, or the like can be used. Besides these single-layer films, a stack of a film containing titanium nitride as its main component and a film containing aluminum as its main component, a stack of three layers of a titanium nitride film, a film containing aluminum as its main component, and a titanium nitride film, or the like can be used. When a stacked-layer structure is employed, the first electrode 613 can have low resistance as wiring, obtain favorable ohmic contact, and moreover function as an anode.

The EL layer 616 is formed by various methods such as an evaporation method using an evaporation mask, an inkjet method, or a spin coating method. The EL layer 616 includes a quinoxaline derivative of the present invention shown in Embodiment Mode 1. As another material for forming the EL layer 616, a low molecular material, a middle molecular material (including oligomer and dendrimer) or a high molecular material may be used.

The second electrode 617 which is fowled over the EL layer 616 and functions as a cathode is preferably formed of a material with a low work function (Al, Mg, Li, Ca, or an alloy or compound thereof, e.g., MgAg, MgIn, AlLi, LiF, or CaF$_2$). When light generated in the EL layer 616 passes through the second electrode 617, the second electrode 617 is preferably formed by a stack of a thin metal film and a transparent conductive film (ITO, indium oxide including 2 to 20 wt % of zinc oxide, indium tin oxide including silicon or silicon oxide, zinc oxide (ZnO), or the like).

When the sealing substrate 604 and the element substrate 610 are attached to each other with the sealant 605, a light-emitting element 618 described as in Embodiment Modes 2 to 5 is provided in the space 607 surrounded by the element substrate 610, the sealing substrate 604, and the sealant 605. The space 607 is filled with a filler, which may be an inert gas (such as nitrogen or argon) or the sealant 605.

The sealant 605 is preferably formed of an epoxy-based resin. It is desirable that the material of the sealant 605 preferably allows as little moisture and oxygen as possible to penetrate. As the sealing substrate 604, a plastic substrate formed of FRP (Fiberglass-Reinforced Plastics), PVF (polyvinyl fluoride), Myler (registered trademark), polyester, acrylic, or the like can be used, in addition to a glass substrate or a quartz substrate.

As described above, the light-emitting device manufactured by the quinoxaline derivative of the present invention can be obtained.

The light-emitting device of the present invention uses the aromatic amine compound shown in Embodiment Mode 1; therefore, the light-emitting device can have favorable characteristics. Specifically, the light-emitting device can have high heat resistance.

Figure 5A:
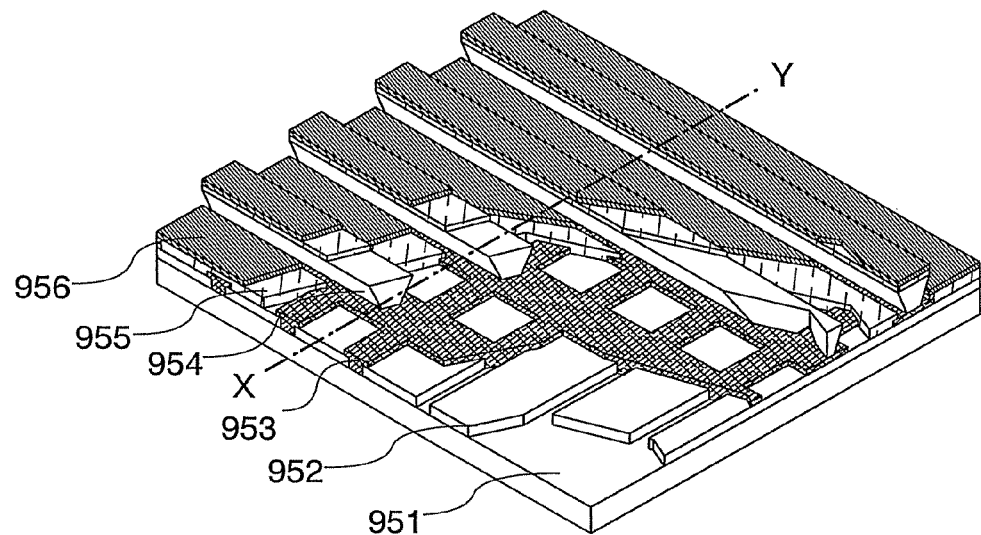
FIGS. 5A and 5B illustrate a light-emitting device of the present invention.
Figure 5B:
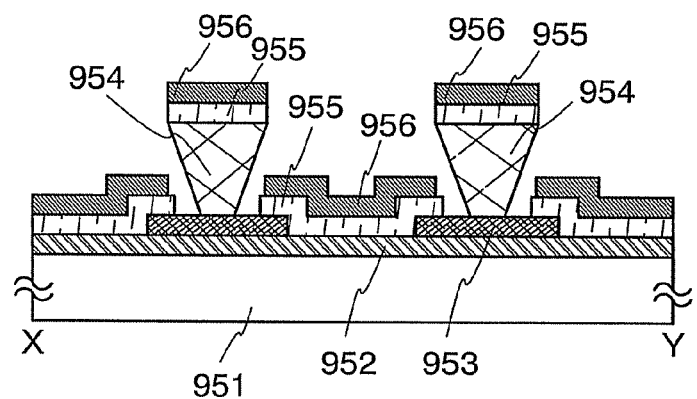

This embodiment mode has described the active light-emitting device in which the driving of the light-emitting element is controlled by a transistor. However, a passive light-emitting device may be adopted. FIG. 5 is a perspective view of a passive light-emitting device manufactured by applying the present invention. In FIG. 5, an EL layer 955 is provided over a substrate 951 and between an electrode 952 and an electrode 956. End portions of the electrode 952 are covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a narrow side is trapezoidal, and a base (a side facing in a similar direction to a plane direction of the insulating layer 953 and being in contact with the insulating layer 953) is shorter than an upper side (a side facing in a similar direction to the plane direction of the insulating layer 953 and not being in contact with the insulating layer 953). A defect of the light-emitting element due to static electricity or the like can be prevented by providing the partition layer 954 in this manner. In addition, the passive light-emitting device can also have excellent heat resistance when it includes the light-emitting element of the present invention.

Embodiment Mode 7

This embodiment mode explains electronic devices of the present invention which includes the light-emitting device described in Embodiment Mode 4 as its component. The electronic devices of the present invention include quinoxaline derivatives of the present invention described in Embodiment Mode 1 and have display portions with high heat resistance.

Examples of the electronic devices having the light-emitting elements manufactured using quinoxaline derivatives of the present invention include the following: cameras such as video cameras or digital cameras, goggle type displays, navigation systems, sound reproducing devices (car audio systems, audio components, or the like), computers, game machines, mobile information terminals (mobile computers, cellular phones, mobile game machines, electronic books, or the like), image reproducing devices having recording media (specifically, a device which reproduces content of a recording medium such as a digital versatile disc (DVD) and has a display device for displaying the image), and the like. Specific examples of these electronic devices are shown in FIGS. 6A to 6D.

Figure 6A:
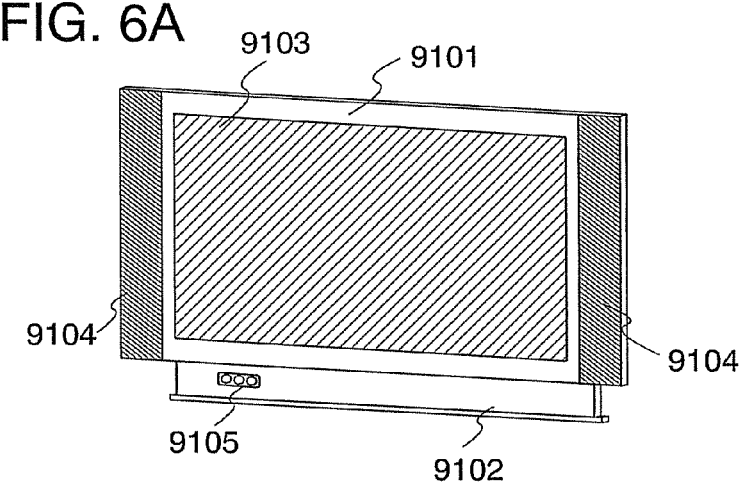
FIGS. 6A to 6D illustrate electronic devices of the present invention.

FIG. 6A illustrates a television device according to the present invention which includes a housing 9101, a support base 9102, a display portion 9103, speaker portions 9104, a video input terminal 9105, and the like. In this television device, the display portion 9103 includes light-emitting elements similar to those described in Embodiment Modes 2 to 4, which are arranged in matrix. The light-emitting element has a feature of high heat resistance. The display portion 9103 which includes the light-emitting element also has a similar feature, and thus the television device can also have high heat resistance.

Figure 6B:
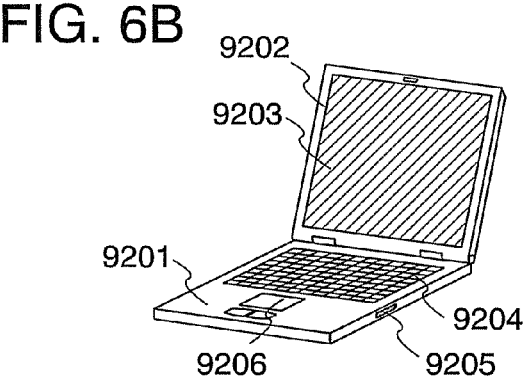

FIG. 6B illustrates a computer according to the present invention which includes a main body 9201, a housing 9202, a display portion 9203, a keyboard 9204, an external connection port 9205, a pointing device 9206, and the like. In this computer, the display portion 9203 includes light-emitting elements similar to those described in Embodiment Modes 2 to 4, which are arranged in matrix. The light-emitting element has a feature of high heat resistance. The display portion 9203 which includes the light-emitting element has a similar feature, and thus the computer can also have high heat resistance.

Figure 6C:
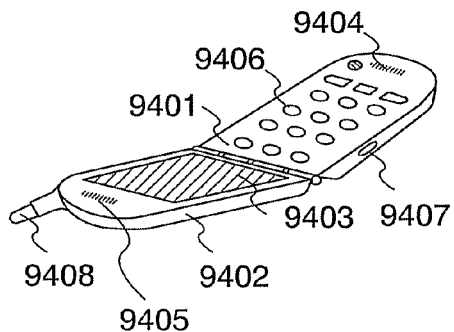

FIG. 6C illustrates a cellular phone according to the present invention which includes a main body 9401, a housing 9402, a display portion 9403, an audio input portion 9404, an audio output portion 9405, operation keys 9406, an external connection port 9407, an antenna 9408, and the like. In this cellular phone, the display portion 9403 includes light-emitting elements similar to those described in Embodiment Modes 2 to 4, which are arranged in matrix. The light-emitting element has a feature of high heat resistance, and thus the cellular phone can also have high heat resistance.

Figure 6D:
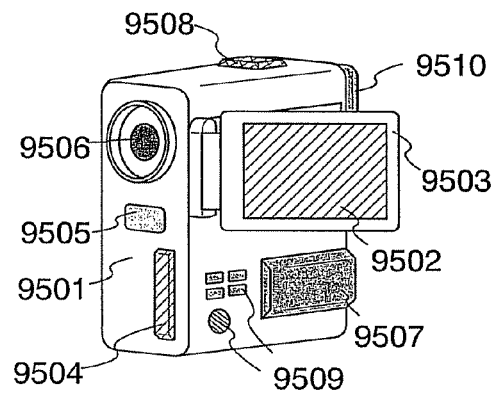

FIG. 6D illustrates a camera according to the present invention which includes a main body 9501, a display portion 9502, a housing 9503, an external connection port 9504, a remote control receiving portion 9505, an image receiving portion 9506, a battery 9507, an audio input portion 9508, an operation key 9509, an eye piece portion 9510, and the like. In this camera, the display portion 9502 includes light-emitting elements similar to those described in Embodiment Modes 2 to 4, which are arranged in matrix. The light-emitting element has a feature of high heat resistance. The display portion 9502 which includes the light-emitting element also has similar features, and thus the camera can also have high heat resistance.

As described above, the applicable range of the light-emitting device of the present invention is so wide that the light-emitting device can be applied to electronic devices in various fields. By the use of a quinoxaline derivative of the present invention, electronic devices including display portions with high heat resistance can be provided.

In addition, the light-emitting device of the present invention can also be used as an illumination apparatus. One mode of using the light-emitting element of the present invention as an illumination apparatus is explained with reference to FIG. 7.

Figure 7:
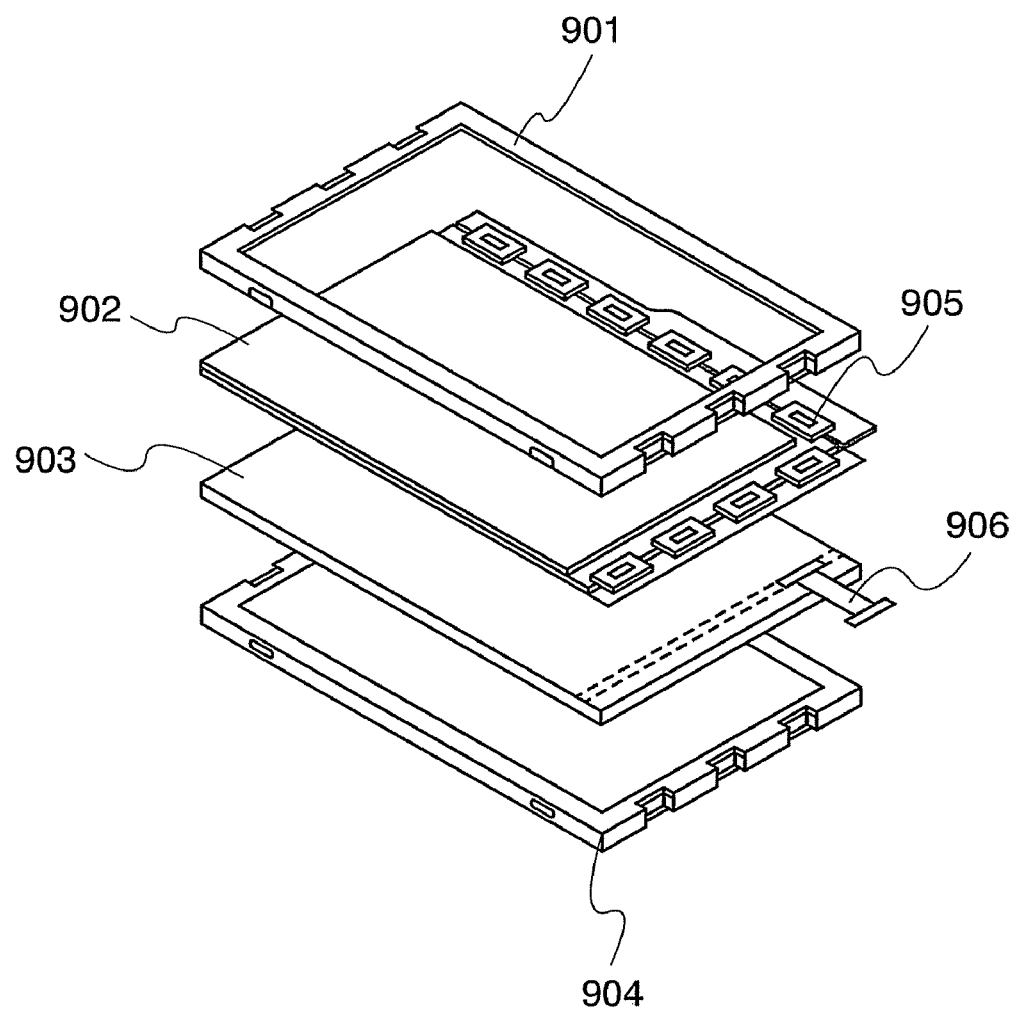
FIG. 7 illustrates an electronic device of the present invention.

FIG. 7 illustrates an example of a liquid crystal display device using the light-emitting device of the present invention as a backlight. The liquid crystal display device shown in FIG. 7 includes a housing 901, a liquid crystal layer 902, a backlight 903, and a housing 904. The liquid crystal layer 902 is connected to a driver IC 905. The light-emitting device of the present invention is used as the backlight 903, to which current is supplied through a terminal 906.

By using the light-emitting device of the present invention as a backlight of the liquid crystal display device, the backlight can have high heat resistance. Since the light-emitting device of the present invention is a surface light-emitting illumination apparatus and can be formed to have a large area, a larger-area backlight can be obtained and a larger-area liquid crystal display device can also be obtained.

EXAMPLE 1

Example 1 will concretely describe a synthesis example of 2,3-bis[4-(3,6-diphenylcarbazol-9-yl)phenyl]quinoxaline (DPCPQ) which is a quinoxaline derivative of the present invention and is represented by the following structural formula (5).

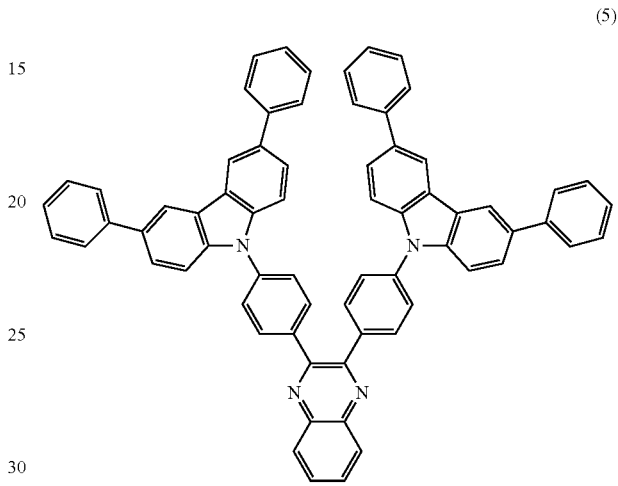

(5)

[Step 1]

A synthesis method of 2,3-bis(4-bromophenyl)quinoxaline is described. A synthesis scheme of 2,3-bis(4-bromophenyl)quinoxaline is represented by (a-1).

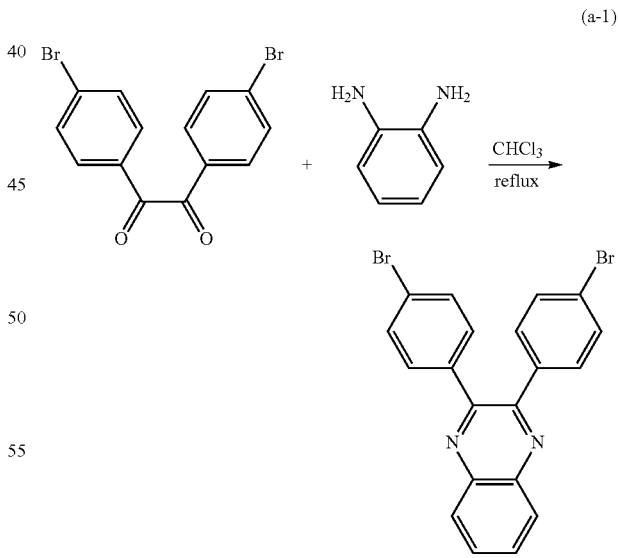

(a-1)

30.2 g of 4,4'-dibromobenzil (82.0 mmol), 9.31 g of 1,2-phenylenediamine (86.1 mmol), and 300 mL of chloroform were put into a 500 mL three-necked flask. This reaction solution was refluxed for five hours at 80° C. under a nitrogen gas stream. After the reaction, the reaction solution was cooled to room temperature and washed with water. A water layer was extracted with chloroform, the extracted solution and an organic layer were dried by magnesium sulphate. After drying, the mixture was filtrated by suction to concentrate the filtrate. The obtained solid was dissolved in toluene and this solution was filtrated by suction through Florisil, celite, and alumina. The filtrate was condensed, and 30 g of an objective matter, a white powder solid, 2,3-bis(4-bromophenyl)quinoxaline was obtained at the yield 99%.

[Step 2]

A synthesis method of 3,6-diphenylcarbazole is described. A synthesis scheme of 3,6-diphenylcarbazole is represented by (a-2).

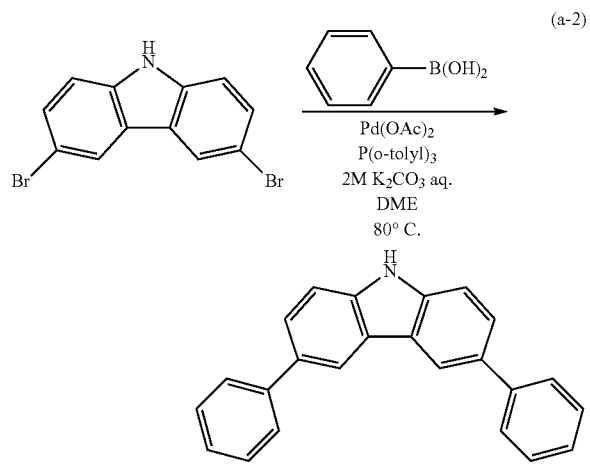

6.5 g of 3,6-dibromocarbazole (20 mmol), 5.0 g of phenyl-boron acid (41 mmol), 93 mg of palladium(II) acetate (0.40 mmol), 610 mg of tri(ortho-tolyl)phosphine (1.9 mmol) were put into a 200 mL three-necked flask, and then, the inside of the flask was substituted by nitrogen. Into the mixture, 50 ml of ethyleneglycol dimethylether (abbreviation: DME), and 25 mL of a potassium carbonate water solution (2.0 mol/L) were added. This mixture was refluxed for 3.5 hours at 80° C. After the reaction, the reaction mixture was washed with water and a water layer was extracted with toluene. The extracted solution and an organic layer were washed with a saturated saline, and dried by magnesium sulphate. The mixture was naturally filtrated. The filtrate was condensed, and 4.1 g of an objective matter, a white powder solid was obtained at the yield 63%.

[Step 3]

A synthesis method of 2,3-bis[4-(3,6-diphenylcarbazol-9-yl)phenyl]quinoxaline (DPCPQ) is described. A synthesis scheme of DPCPQ was represented by (a-3).

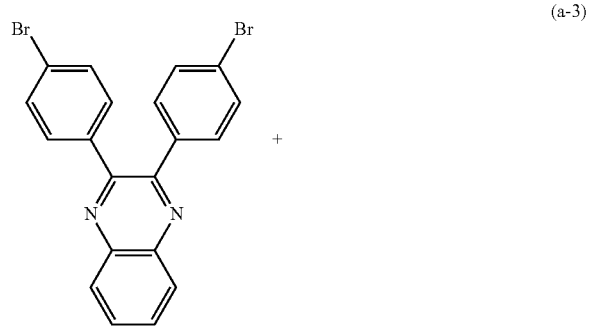

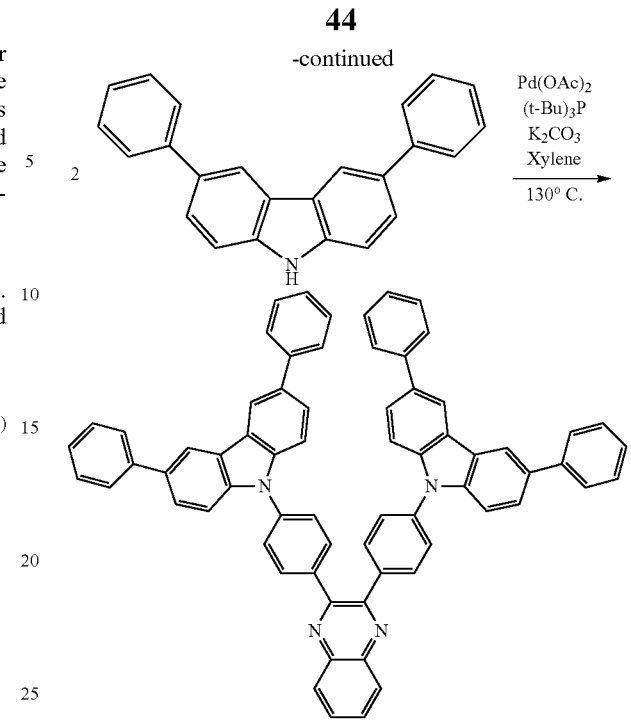

2.3 g of 2,3-bis(4-bromophenyl)quinoxaline (6.1 mmol), 4.3 g of 3,6-diphenyl carbazole (14 mmol), 0.061 g of palladium(II) acetate (0.27 mmol), 5.6 g of potassium carbonate (41 mmol) were put into a 200 mL three-necked flask, and the inside was substituted by nitrogen. Into this mixture, 50 mL of xylene, and 1.7 g of tri(tert-butyl)phosphine (10% hexane solution) (0.81 mmol) were added. This mixture was stirred for 12 hours at 130° C. After the reaction, a precipitate of the reaction mixture was filtrated by suction to be collected. The obtained solid was dissolved in chloroform and this solution was filtrated by suction through Florisil, celite, and alumina. The filtrate was condensed, the obtained solid was recombined with a mixed solvent of chloroform and hexane to be recrystallized and 3.2 g of an objective matter, a lemon-yellow powder solid was obtained at the yield 57%. It was confirmed by a nuclear magnetic resonance method (NMR) that this compound was DPCPQ. 3.2 g of the obtained DPCPQ was refined by sublimation at 380° C. under the following conditions: the pressure was 5.6 Pa, and an argon flow rate was 3.0 mL/min. 0.8 g of DPCPQ was collected and the collection rate was 25%.

Figure 8A:
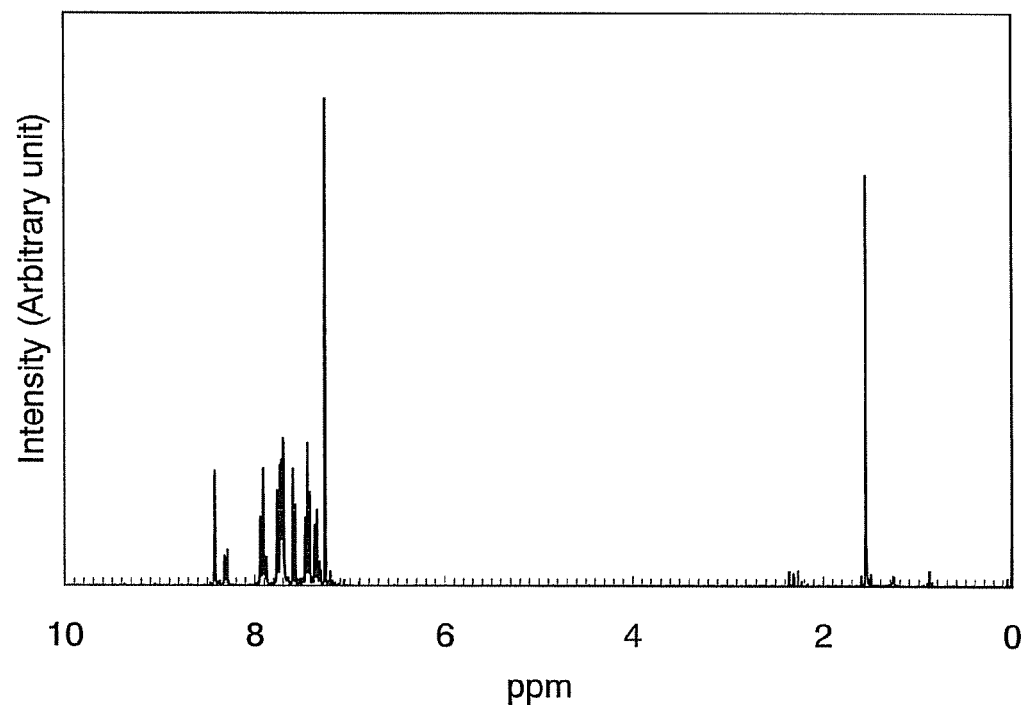
FIGS. 8A and 8B are $^1$H NMR charts of 2,3-bis[4-(3,6-diphenylcarbazol-9-yl)phenyl]quinoxaline which is a quinoxaline derivative of the present invention.
Figure 8B:
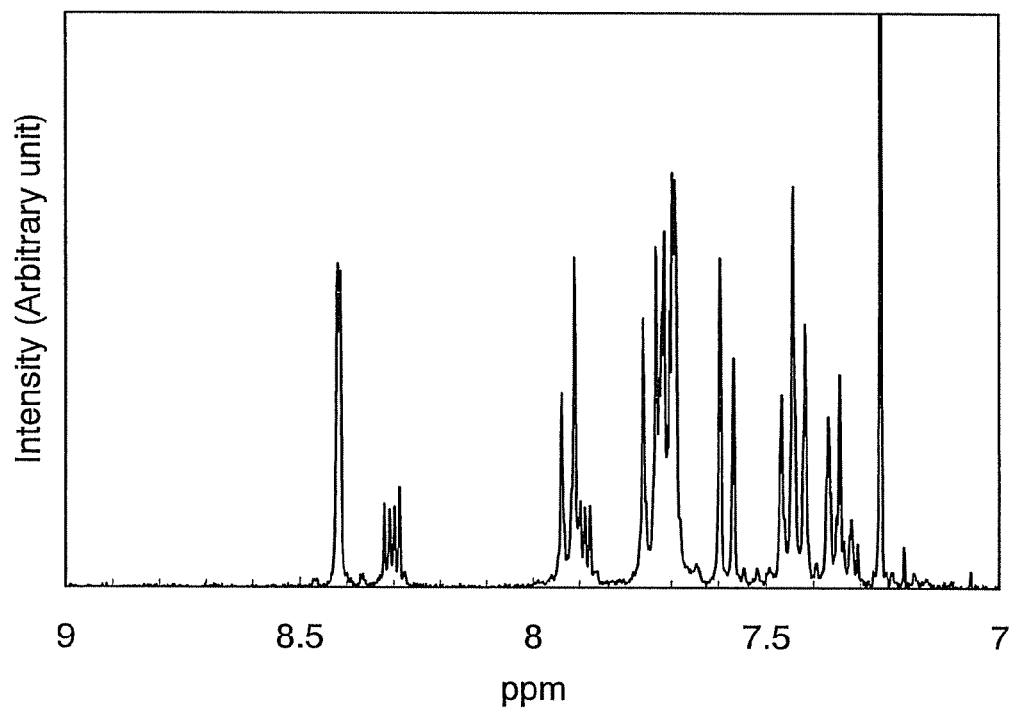

The analysis result of DPCPQ by proton nuclear magnetic resonance spectrometry ($^1$HNMR) was as follows. $^1$HNMR (CDCl$_3$, 300 MHz): δ=7.32-7.37 (m, 4H), 7.42-7.47 (m, 8H), 7.57-7.60 (m, 4H), 7.69-7.81 (m, 17H), 7.88-7.94 (m, 6H), 8.29-8.32 (m, 2H), 8.42-8.42 (m, 3H). FIG. 8A is a $^1$HNMR chart of DPCPQ, and FIG. 8B is an enlarged $^1$HNMR chart of DPCPQ in 7.0 to 9.0 ppm.

Figure 9:
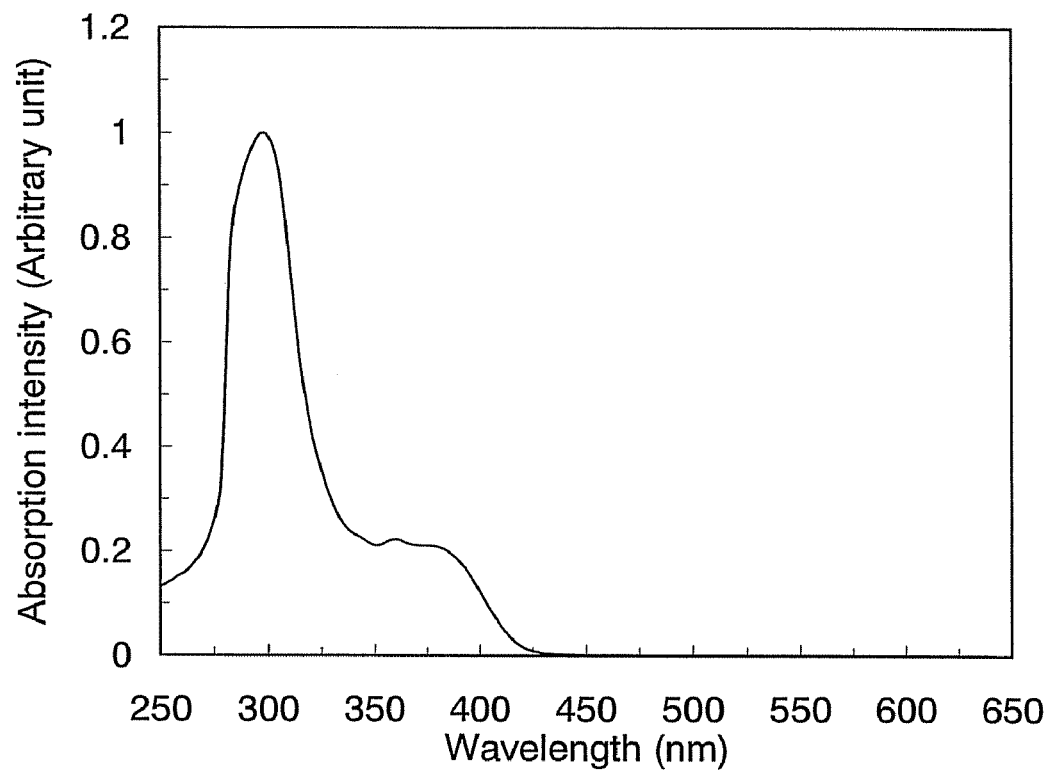
FIG. 9 is a graph showing an absorption spectrum in a toluene solution of 2,3-bis[4-(3,6-diphenylcarbazol-9-yl)phenyl]quinoxaline which is a quinoxaline derivative of the present invention.
Figure 10:
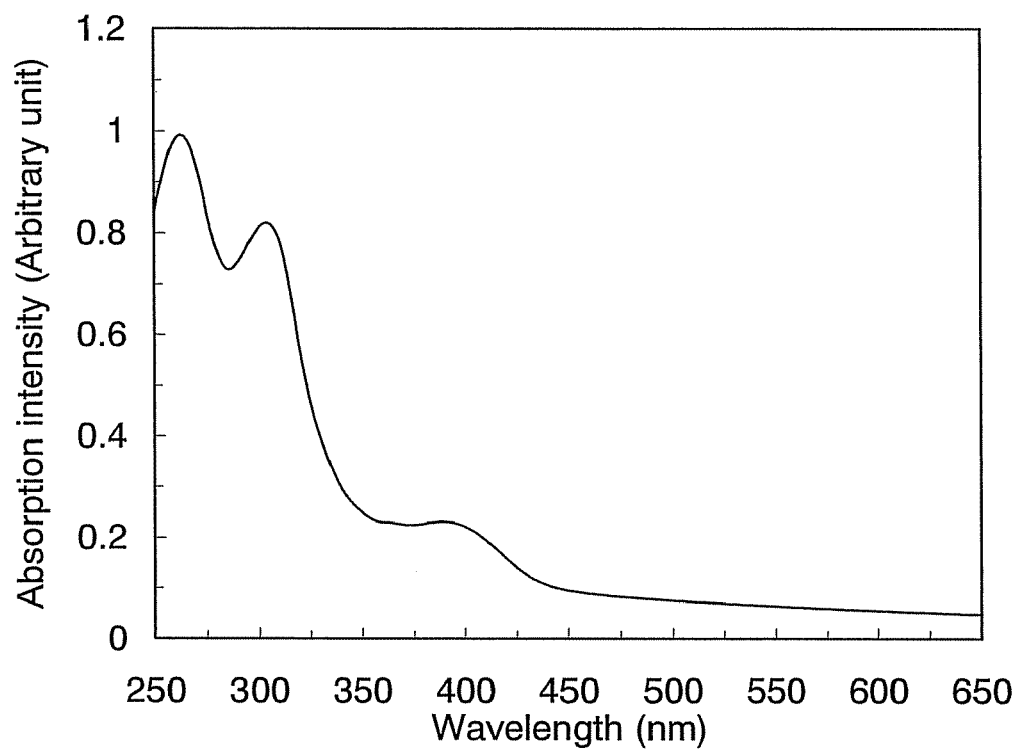
FIG. 10 is a graph showing an absorption spectrum in a thin film state of 2,3-bis[4-(3,6-diphenylcarbazol-9-yl)phenyl]quinoxaline which is a quinoxaline derivative of the present invention.

FIG. 9 illustrates an absorption spectrum of a toluene solution of DPCPQ. FIG. 10 illustrates an absorption spectrum of a thin film of DPCPQ. A peak is at 360 nm in the toluene solution, and a peak is at 388 nm in the thin film state.

Figure 11:
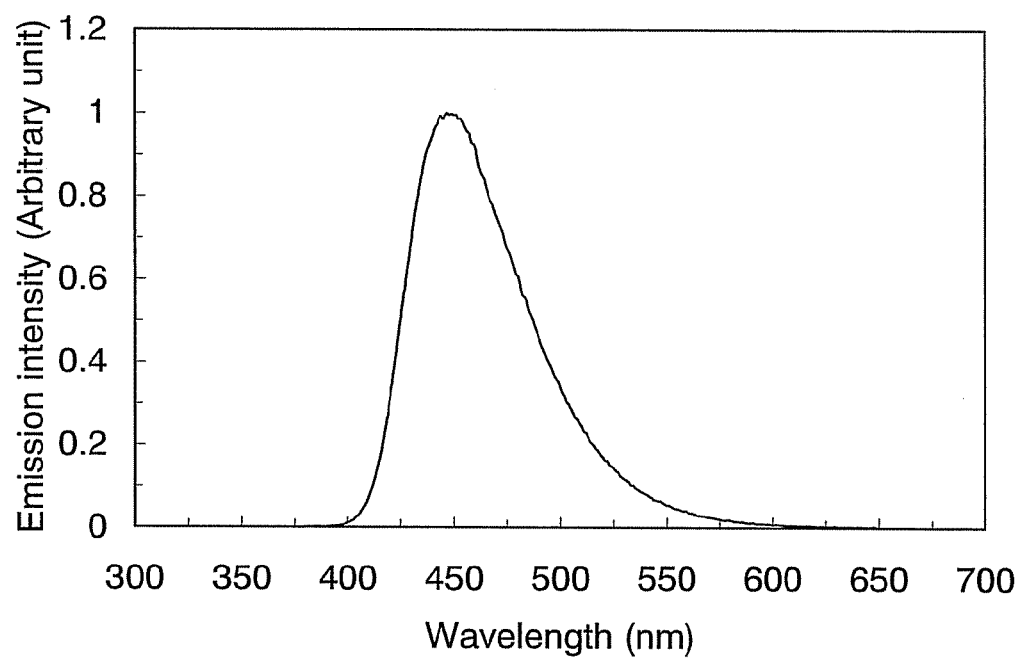
FIG. 11 is a graph showing an emission spectrum in a toluene solution of 2,3-bis[4-(3,6-diphenylcarbazol-9-yl)phenyl]quinoxaline which is a quinoxaline derivative of the present invention.
Figure 12:
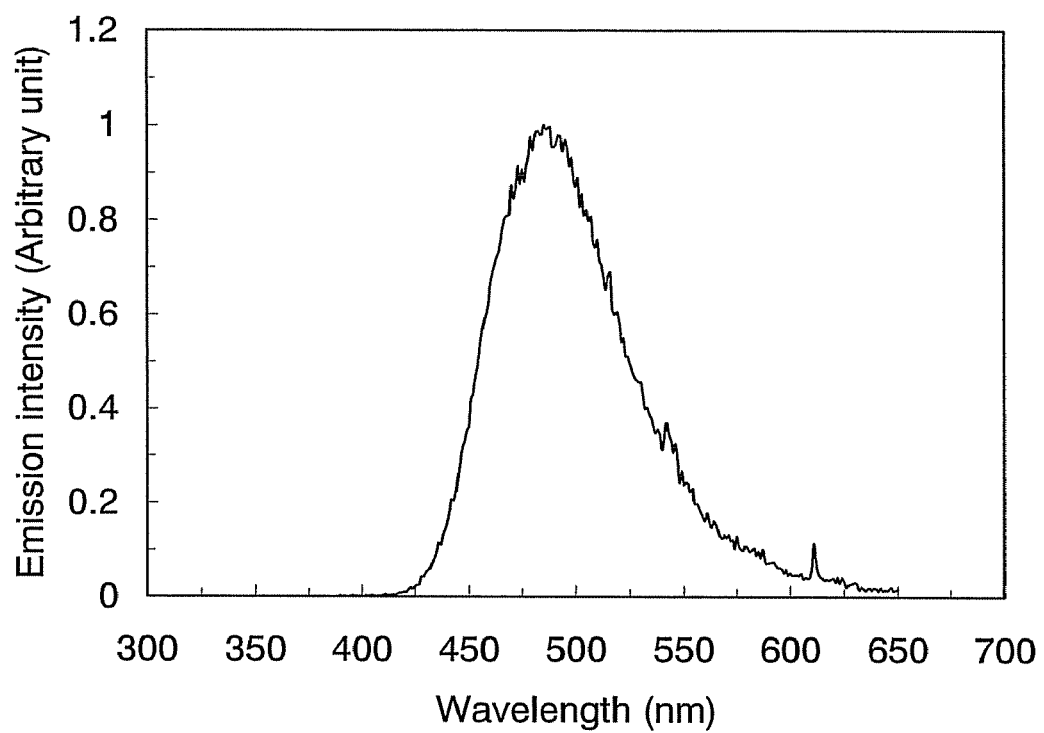
FIG. 12 is a graph showing an emission spectrum in a thin film state of 2,3-bis[4-(3,6-diphenylcarbazol-9-yl)phenyl]quinoxaline which is a quinoxaline derivative of the present invention.

An emission spectrum of DPCPQ in the toluene solution which was excited by an ultraviolet ray with a wavelength of 360 nm is illustrated in FIG. 11. It is found that the light emission maximum is at 448 nm in the toluene solution. An emission spectrum of DPCPQ in the thin film state (solid) which was excited by an ultraviolet ray with a wavelength of 388 nm is illustrated in FIG. 12. It is found that the light emission maximum is at 485 nm in the toluene solution in FIG. 12.

In addition, the HOMO level in the thin film state was −5.75 eV, which was measured by a photoelectron spectrometer (AC-2, manufactured by Riken Keiki Co., Ltd.) Further, an optical energy gap was obtained from a Tauc plot assuming direct transition by using the data of the absorption spectrum in FIG. 10. The energy gap was 2.76 eV. Therefore, a LUMO level was −2.99 eV.

Experimental Comparative Example

Thermophysical properties of DPCPQ which is the above synthesized compound of the present invention were measured and compared with 2,3-bis[4-(carbazol-9-yl)phenyl] quinoxaline (abbreviation: CzQn) represented by the structural formula (101). According to the structural formula (101), a comparative object, CzQn is a compound disclosed in Reference 1, in which phenyl groups coupled with the third and sixth positions of the carbazolyl group of DPCPQ are all hydrogen atoms. As the measurement apparatus, a differential scanning calorimeter (Pyris 1 DSC, manufactured by PerkinElmer, Inc.) was used to measure a melting point.

(101)

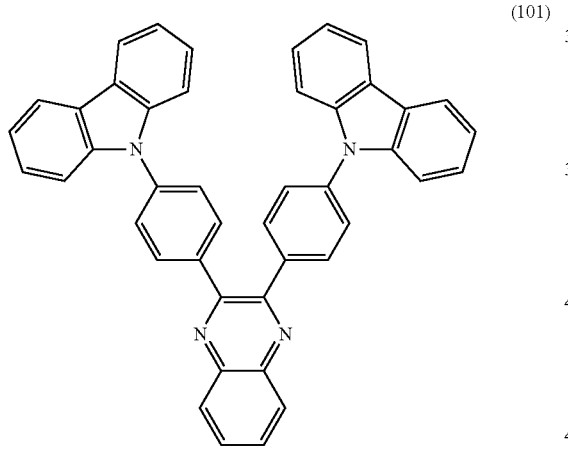

Figure 18:
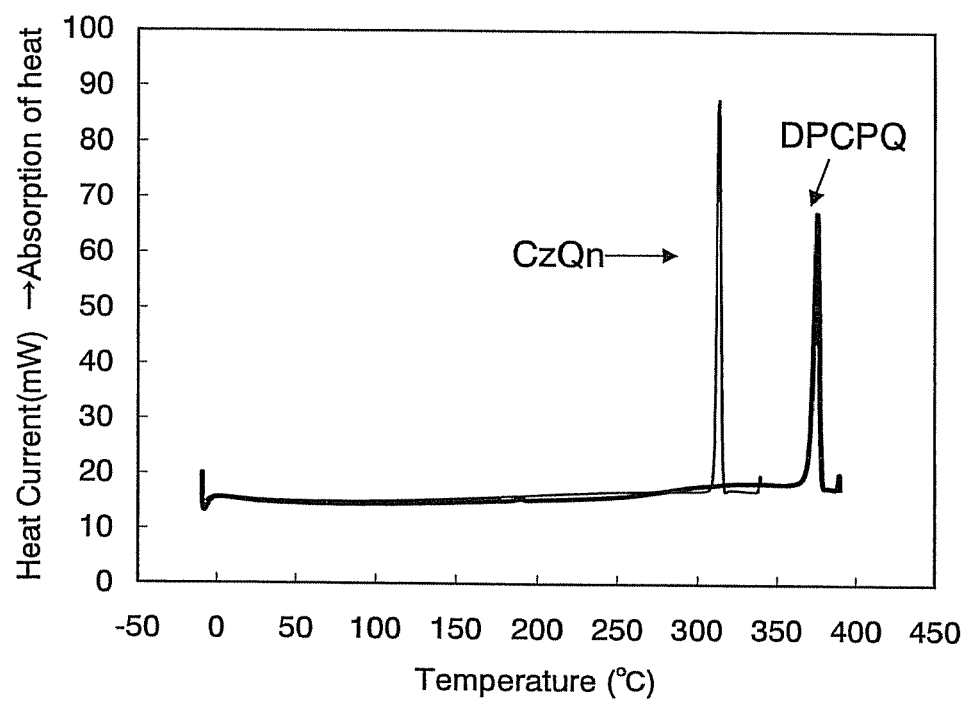
FIG. 18 is a DSC chart of 2,3-bis[4-(3,6-diphenylcarbazol-9-yl)phenyl]quinoxaline.

FIG. 18 illustrate a DSC chart obtained when DPCPQ was heated from −10° C. to 390° C. at a rising temperature 40° C./min and a DSC chart obtained when CzQn was heated from −10° C. to 340° C. at a rising temperature 40° C./min. From these charts, a peak of the melting point of DPCPQ was observed around 370° C., while a peak of the melting point of CzQn was observed around 310° C.

As described above, it is found that heat resistance can be enhanced, by the concept of the present invention, i.e., introduction of a phenyl group into the third and sixth positions of a carbazolyl group.

EXAMPLE 2

Figure 17:
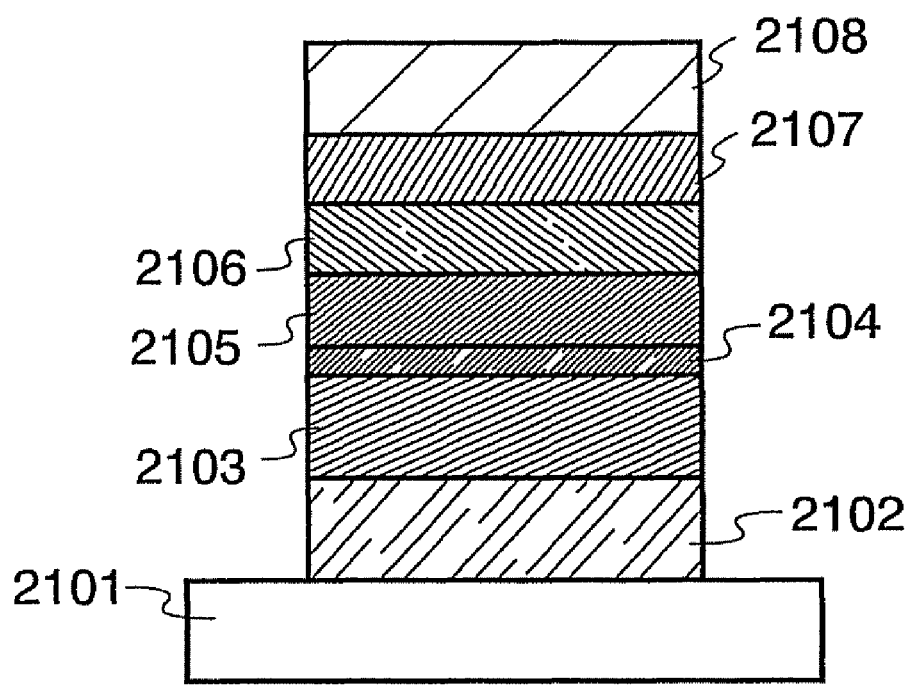
FIG. 17 illustrates a light-emitting element of the present invention.

Example 2 describes a light-emitting element of the present invention with reference to FIG. 17. Chemical formulas of materials in this example are represented below.

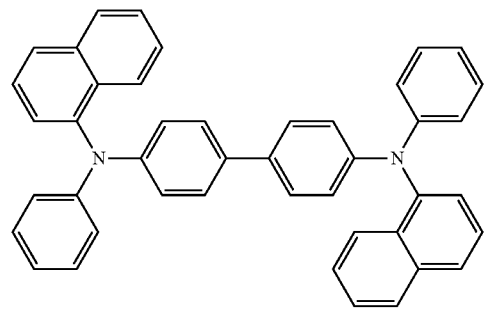

NPB

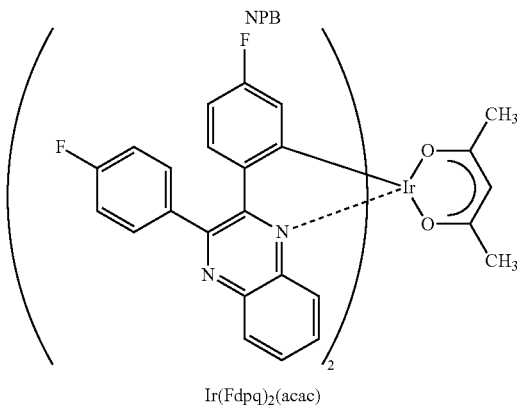

Ir(Fdpq)$_2$(acac)

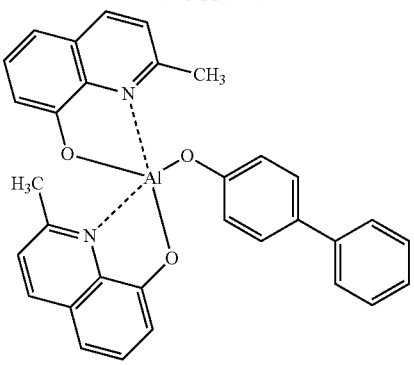

BAlq

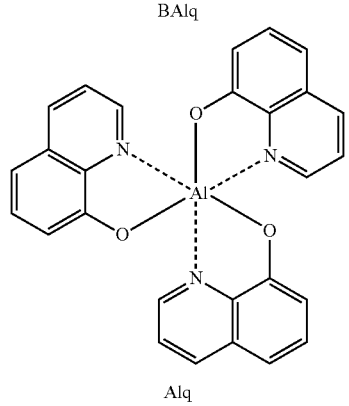

Alq

A method for manufacturing of a light-emitting element in this example is described below.

First, indium tin oxide including silicon oxide was formed over a glass substrate 2101 by a sputtering method to form a first electrode 2102. The first electrode 2102 has a film thickness of 110 nm and an electrode area of 2 mm×2 mm.

Next, the substrate over which the first electrode was formed was fixed to a substrate holder provided in a vacuum evaporation apparatus in such a way that a surface of the substrate having the first electrode faced downward. The inside of the vacuum evaporation apparatus was evacuated and the pressure was reduced to be about $10^{-4}$ Pa. Then, NPB and molybdenum(VI) oxide were co-evaporated to form a layer 2103 containing a composite material over the first electrode 2102. The film thickness of the layer 2103 was 50 nm, and the weight ratio between NPB and molybdenum(VI) oxide was set 4:1 (=NPB:molybdenum oxide). It is to be noted that the co-evaporation method is an evaporation method in which evaporation is performed from plural evaporation sources at the same time in one process chamber.

Subsequently, a hole-transporting layer 2104 having a thickness of 10 nm was formed over the layer 2103 containing a composite material by using an evaporation method using resistance heating.

Further, a light-emitting layer 2105 having a thickness of 30 nm was formed over the hole-transporting layer 2104 by co-evaporating 2,3-bis[4-(3,6-diphenylcarbazol-9-yl)phenyl]quinoxaline (DPCPQ) represented by the structural formula (5) of the present invention and (acetylacetonato)bis[2,3-bis(4-fluorophenyl)quinoxalinato iridium(III) (Ir(Fdpq)$_2$(acac)). Here, the weight ratio between DPCPQ and Ir(Fdpq)$_2$(acac) was adjusted to be 1:0.05 (=DPCPQ:Ir(Fdpq)$_2$(acac)).

After that, an electron-transporting layer 2106 of BAlq having a thickness of 10 nm was formed over the light-emitting layer 2105 by an evaporation method using resistance heating.

Moreover, an electron-injecting layer 2107 having a thickness of 50 nm was formed by co-evaporating Alq and lithium over the electron-transporting layer 2106. Here, the weight ratio between Alq and lithium was adjusted to be 1:0.01 (=Alq:lithium).

Then, a second electrode 2108 having a thickness of 200 nm was formed of aluminum over the electron-injecting layer 2107 by an evaporation method using resistance heating. Thus, the light-emitting element of Example 2 was manufactured.

Figure 13:
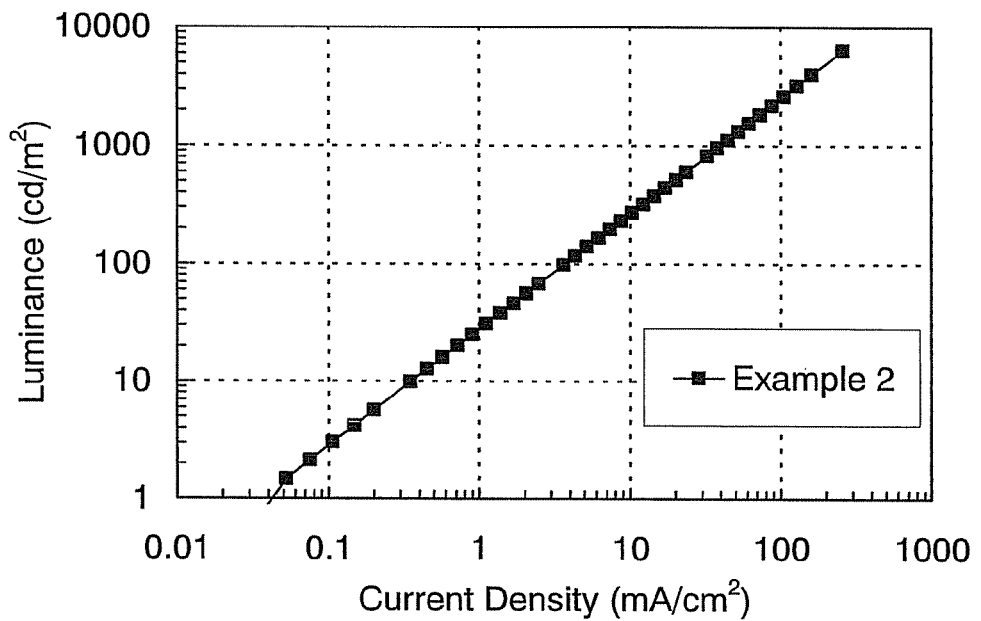
FIG. 13 is a graph showing luminance-current density characteristics of a light-emitting element in Example 2.
Figure 14:
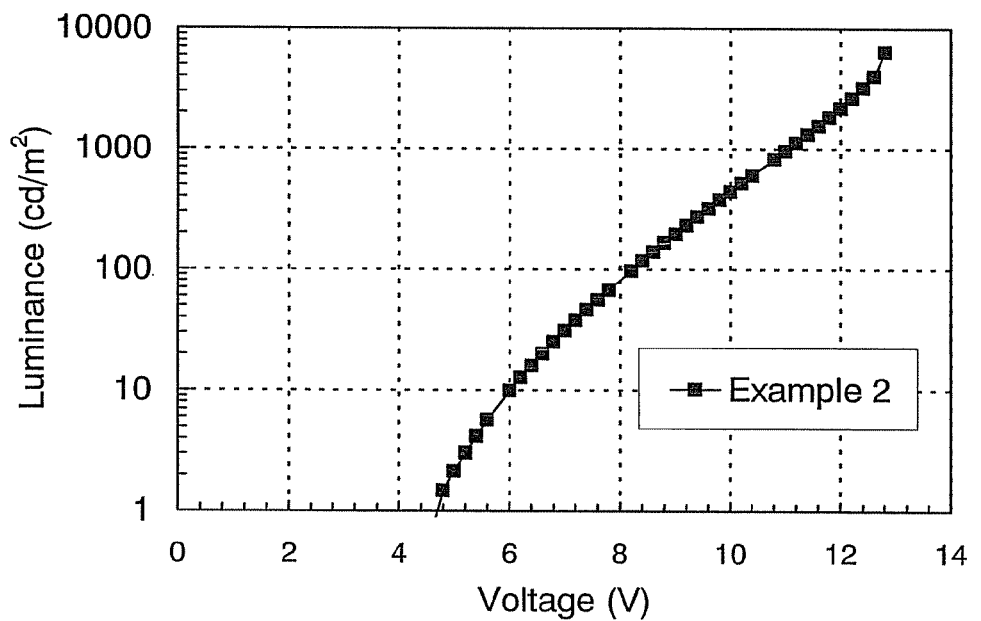
FIG. 14 is a graph showing luminance-voltage characteristics of the light-emitting element in Example 2.
Figure 15:
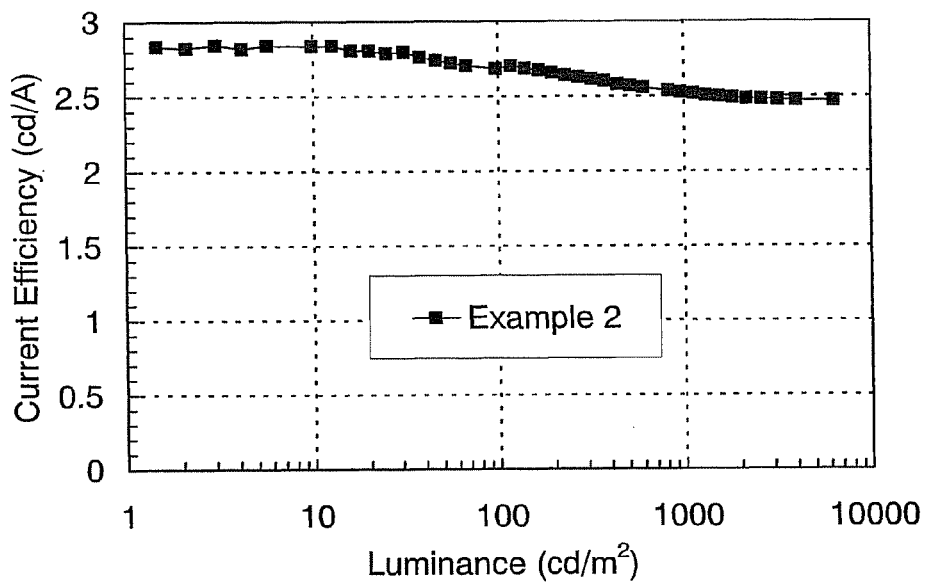
FIG. 15 is a graph showing current efficiency-luminance of the light-emitting element in Example 2.
Figure 16:
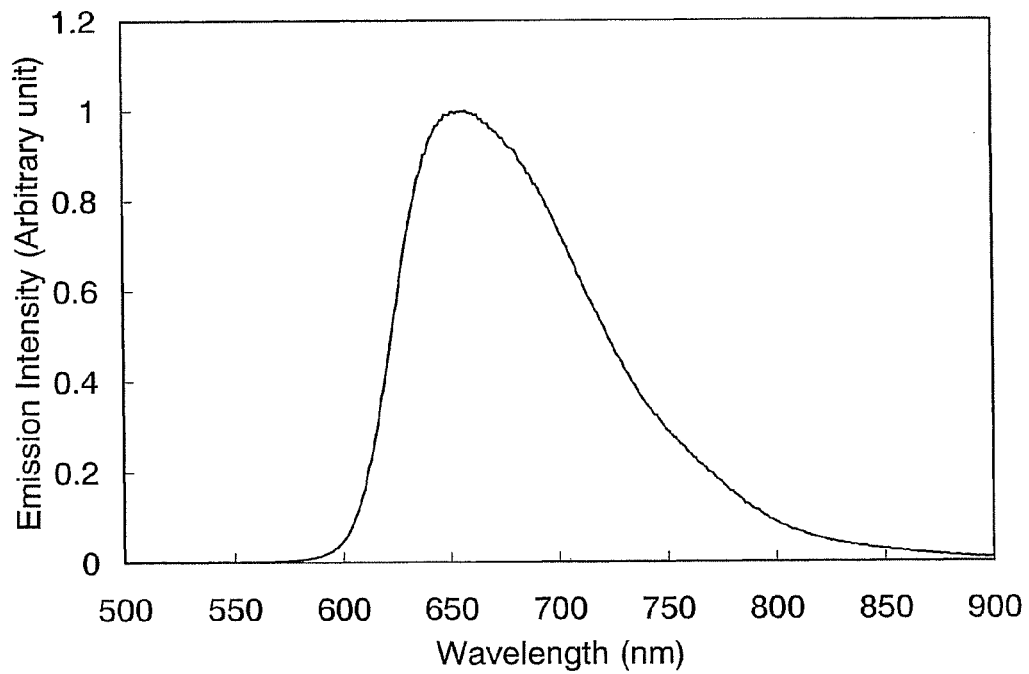
FIG. 16 is a graph showing an emission spectrum of the light-emitting element in Example 2.

FIGS. 13, 14 and 15 illustrate current density-luminance characteristics, voltage-luminance characteristics, and luminance-current efficiency of the light-emitting element in Example 2, respectively. FIG. 16 illustrates an emission spectrum when 1 mA of current flows. In the light-emitting element of Example 2, a voltage necessary to obtain luminance of 958 cd/m$^2$ was 11.0 V, and the current at that time was 1.52 mA (current density was 37.9 mA/cm$^2$), and the CIE chromaticity coordinates were (x=0.71, y=0.28). The current efficiency was 2.5 cd/A, and the power efficiency was 0.72 1 m/W at that time.

In this manner, a quinoxaline derivative of the present invention and an organometallic complex are combined, so that a red phosphorescent element can be provided.

This application is based on Japanese Patent Application serial No. 2006-266159 filed in Japan Patent Office on Sep. 29, 2006, the entire contents of which are hereby incorporated by reference.

What is claimed is:

1. A light-emitting device comprising:
a first electrode;
a first light-emitting unit over the first electrode;
a charge-generating layer over the first light-emitting unit;
a second light-emitting unit over the charge-generating layer; and
a second electrode over the second light-emitting unit, wherein at least one of the first light-emitting unit and the second light-emitting unit comprises a quinoxaline derivative represented by a general formula (1);

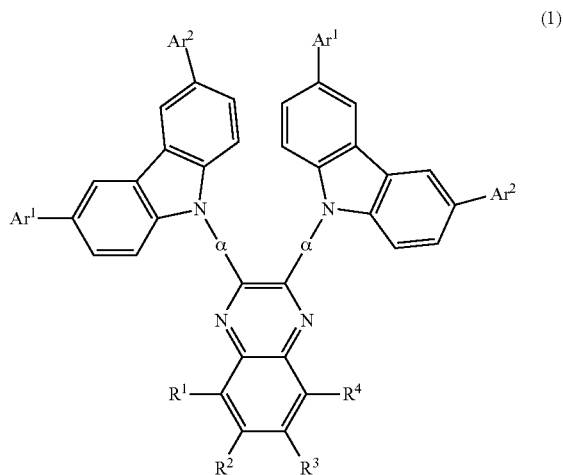

wherein $R^1$ to $R^4$ each represent one of a hydrogen atom, an alkyl group having 1 to 4 carbon atoms, and an aryl group having 6 to 25 carbon atoms,
wherein $Ar^1$ and $Ar^2$ each are represented by a general formula (2),

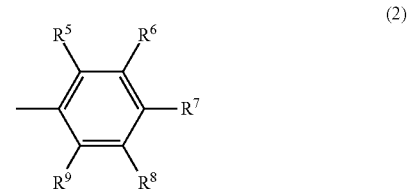

wherein $R^5$ to $R^9$ each represent one of a hydrogen atom, an alkyl group having 1 to 4 carbon atoms, and an aryl group having 6 to 15 carbon atoms, and
wherein α represents an arylene group having 6 to 25 carbon atoms.

2. The light-emitting device according to claim 1, wherein α represents a phenylene group.

3. The light-emitting device according to claim 1, wherein α represents a 1,2-phenylene group or a 1,3-phenylene group.

4. The light-emitting device according to claim 1, wherein α represents a phenylene group, wherein $Ar^1$ and $Ar^2$ each represent a phenyl group, and wherein $R^1$ to $R^4$ each represent a hydrogen atom.

5. The light-emitting device according to claim 1, wherein α represents a 1,4-phenylene group, wherein $Ar^1$ and $Ar^2$ each represent a phenyl group, and wherein $R^1$ to $R^4$ each represent a hydrogen atom.

6. The light-emitting device according to claim 1, wherein at least one of the pairs $R^1$ and $R_2$, $R^2$ and $R^3$, and $R^4$ is bound to each other to form a ring.

7. The light-emitting device according to claim 1, wherein the charge-generating layer comprises an organic compound and a metal oxide.

8. The light-emitting device according to claim 1, further comprising one of a fluorescent substance and a phosphorescent substance between the first electrode and the second electrode.

9. The light-emitting device according to claim 1, further comprising a phosphorescent substance between the first electrode and the second electrode,
wherein a peak of an emission spectrum of the phosphorescent substance is located in a range of 560 nm to 700 nm.

10. The light-emitting device according to claim 1, wherein α in the quinoxaline derivative represents an arylene group having 7 to 25 carbon atoms.

11. A lighting device comprising the light-emitting device according to claim 1.

12. A light-emitting device comprising:
a first electrode;
a first light-emitting unit over the first electrode;
a first charge-generating layer over the first light-emitting unit;
a second light-emitting unit over the first charge-generating layer;
a second charge-generating layer over the second light-emitting unit;
a third light-emitting unit over the second charge-generating layer; and
a second electrode over the third light-emitting unit,
wherein at least one of the first light-emitting unit, the second light-emitting unit and the third light-emitting unit comprises a quinoxaline derivative represented by a general formula (1);

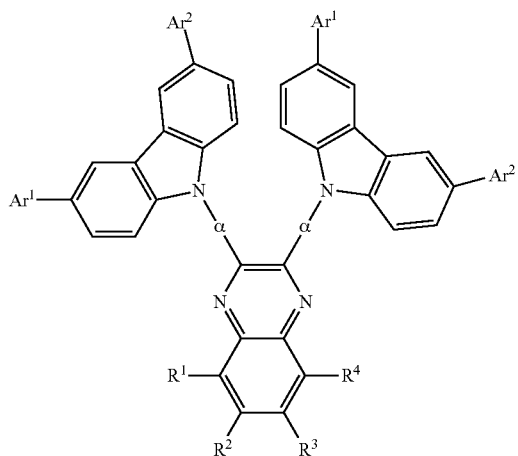

(1)

wherein $R^1$ to $R^4$ each represent one of a hydrogen atom, an alkyl group having 1 to 4 carbon atoms, and an aryl group having 6 to 25 carbon atoms,
wherein $Ar^1$ and $Ar^2$ each are represented by a general formula (2),

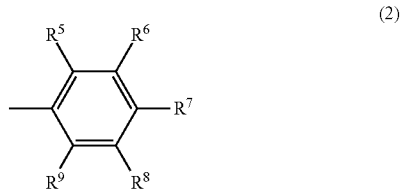

(2)

wherein $R^5$ to $R^9$ each represent one of a hydrogen atom, an alkyl group having 1 to 4 carbon atoms, and an aryl group having 6 to 15 carbon atoms, and
wherein α represents an arylene group having 6 to 25 carbon atoms.

13. The light-emitting device according to claim 12 wherein α represents a phenylene group.

14. The light-emitting device according to claim 12, wherein α represents a 1,2-phenylene group or a 1,3-phenylene group.

15. The light-emitting device according to claim 12, wherein α represents a phenylene group,
wherein $Ar^1$ and $Ar^2$ each represent a phenyl group, and
wherein $R^1$ to $R^4$ each represent a hydrogen atom.

16. The light-emitting device according to claim 12, wherein α represents a 1,4-phenylene group,
wherein $Ar^1$ and $Ar^2$ each represent a phenyl group, and
wherein $R^1$ to $R^4$ each represent a hydrogen atom.

17. The light-emitting device according to claim 12, wherein at least one of the pairs $R^1$ and $R^2$, $R^2$ and $R^3$, and $R^3$ and $R^4$ is bound to each other to form a ring.

18. The light-emitting device according to claim 12, wherein the first charge-generating layer comprises a composite material of an organic compound and a metal oxide.

19. The light-emitting device according to claim 12, wherein the second charge-generating layer comprises a composite material of an organic compound and a metal oxide.

20. The light-emitting device according to claim 12, further comprising one of a fluorescent substance and a phosphorescent substance between the first electrode and the second electrode.

21. The light-emitting device according to claim 12, further comprising a phosphorescent substance between the first electrode and the second electrode,
wherein a peak of an emission spectrum of the phosphorescent substance is located in a range of 560 nm to 700 nm.

22. The light-emitting device according to claim 12, wherein α in the quinoxaline derivative represents an arylene group having 7 to 25 carbon atoms.

23. A lighting device comprising the light-emitting device according to claim 12.

* * * * *